(12) United States Patent
Kircher et al.

(10) Patent No.: US 10,322,194 B2
(45) Date of Patent: Jun. 18, 2019

(54) PARTICLES, METHODS AND USES THEREOF

(71) Applicant: SLOAN-KETTERING INSTITUTE FOR CANCER RESEARCH, New York, NY (US)

(72) Inventors: Moritz Kircher, New York, NY (US); Stefan Harmsen, New York, NY (US); Matthew Wall, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 14/423,946

(22) PCT Filed: Aug. 30, 2013

(86) PCT No.: PCT/US2013/057636
§ 371 (c)(1),
(2) Date: Feb. 25, 2015

(87) PCT Pub. No.: WO2014/036470
PCT Pub. Date: Mar. 6, 2014

(65) Prior Publication Data
US 2015/0258218 A1 Sep. 17, 2015

Related U.S. Application Data

(60) Provisional application No. 61/696,122, filed on Aug. 31, 2012.

(51) Int. Cl.
A61K 49/00 (2006.01)
A61K 51/12 (2006.01)
A61K 49/18 (2006.01)

(52) U.S. Cl.
CPC .......... *A61K 49/0093* (2013.01); *A61K 49/00* (2013.01); *A61K 49/0002* (2013.01); *A61K 49/1878* (2013.01); *A61K 49/1881* (2013.01); *A61K 51/1251* (2013.01)

(58) Field of Classification Search
CPC ................ A61K 49/00; A61K 49/0002; A61K 49/0093; A61K 49/1878; A61K 49/1881; A61K 51/1251; A61K 51/1244
USPC .................................. 424/1.29, 9.1; 427/2.14
See application file for complete search history.

(56) References Cited

U.S. PATENT DOCUMENTS

| | | |
|---|---|---|
| 4,127,329 A | 11/1978 | Chang et al. |
| 4,604,992 A | 8/1986 | Sato |
| 4,669,467 A | 6/1987 | Willett et al. |
| 4,938,205 A | 7/1990 | Nudelman |
| 5,275,594 A | 1/1994 | Baker et al. |
| 5,293,872 A | 3/1994 | Alfano et al. |
| 5,300,097 A | 4/1994 | Lerner et al. |
| 5,306,403 A | 4/1994 | Vo-Dinh |
| 5,491,510 A | 2/1996 | Gove |
| 5,594,497 A | 1/1997 | Ahern et al. |
| 5,609,907 A | 3/1997 | Natan |
| 5,713,364 A | 2/1998 | DeBaryshe et al. |
| 5,721,102 A | 2/1998 | Vo-Dinh |
| 5,813,987 A | 9/1998 | Modell et al. |
| 5,949,388 A | 9/1999 | Atsumi et al. |
| 6,002,471 A | 12/1999 | Quake |
| 6,006,126 A | 12/1999 | Cosman |
| 6,008,889 A | 12/1999 | Zeng et al. |
| 6,019,719 A | 2/2000 | Schulz et al. |
| 6,025,202 A | 2/2000 | Natan |
| 6,127,120 A | 10/2000 | Graham et al. |
| 6,174,291 B1 | 1/2001 | McMahon et al. |
| 6,174,677 B1 | 1/2001 | Vo-Dinh |
| 6,219,137 B1 | 4/2001 | Vo-Dinh |
| 6,242,264 B1 | 6/2001 | Natan et al. |
| 6,251,127 B1 | 6/2001 | Biel |
| 6,254,852 B1 | 7/2001 | Glajch et al. |
| 6,514,767 B1 | 2/2003 | Natan |
| 6,579,726 B1 | 6/2003 | Natan et al. |
| 6,624,886 B2 | 9/2003 | Natan et al. |
| 6,640,130 B1 | 10/2003 | Freeman et al. |
| 6,788,860 B1 | 9/2004 | Treado et al. |
| 6,959,024 B2 | 10/2005 | Paldus et al. |
| 7,076,092 B2 | 7/2006 | Hollars et al. |
| 7,192,778 B2 | 3/2007 | Natan |
| 7,443,489 B2 | 10/2008 | Natan |
| 7,538,859 B2 | 5/2009 | Tearney et al. |
| 7,656,525 B2 | 2/2010 | Zhao et al. |
| 7,738,096 B2 | 6/2010 | Zhao et al. |
| 7,760,352 B2 | 7/2010 | Armstrong et al. |
| 7,826,176 B2 | 11/2010 | Shirotori et al. |
| 7,829,140 B1* | 11/2010 | Zhong ................... A61K 49/183 427/212 |

(Continued)

FOREIGN PATENT DOCUMENTS

| | | |
|---|---|---|
| CN | 101679022 A | 3/2010 |
| CN | 102015020 A | 4/2011 |
| CN | 102175655 A | 9/2011 |
| CN | 102410994 A | 4/2012 |
| CN | 102686181 A | 9/2012 |

(Continued)

OTHER PUBLICATIONS

International Search Report, PCT/US2015/045646, dated Nov. 27, 2015, 5 pages.

(Continued)

*Primary Examiner* — Johann R Richter
*Assistant Examiner* — Courtney A Brown
(74) *Attorney, Agent, or Firm* — Wolf, Greenfield & Sacks, P.C.

(57) ABSTRACT

The present disclosure, among other things, provides a composition including a nanoscale core; a plurality of capping agent entities associated on the core; an outer encapsulant layer; and a plurality of dopant entities distributed at locations selected from the group consisting of: on or within the nanoscale core, on or between capping agent entities, on or within the encapsulating layer, and combinations thereof. Provided technologies can achieve unprecedented levels of dopant entity density and/or surface localization, which, for a SE(R)RS-active agent dopant, results in dramatically improved signal intensity and/or imaging sensitivity.

35 Claims, 29 Drawing Sheets

(56) References Cited

U.S. PATENT DOCUMENTS

| | | | |
|---|---|---|---|
| 8,054,463 B2 | 11/2011 | Morris et al. | |
| 8,320,650 B2 | 11/2012 | Demos et al. | |
| 8,409,862 B2 | 4/2013 | Caulfield et al. | |
| 8,409,863 B2 | 4/2013 | Natan et al. | |
| 8,416,405 B2 | 4/2013 | Panza et al. | |
| 8,497,131 B2 | 7/2013 | Natan et al. | |
| 8,568,878 B2 | 10/2013 | Wilson et al. | |
| 8,771,978 B2 | 7/2014 | Ragan | |
| 8,795,628 B2 | 8/2014 | Gambhir et al. | |
| 8,918,161 B2 | 12/2014 | Natan et al. | |
| 9,086,533 B1 | 7/2015 | Wach | |
| 9,295,391 B1 | 3/2016 | Tearney et al. | |
| 9,561,292 B1 | 2/2017 | Vo-Dinh et al. | |
| 10,105,456 B2 | 10/2018 | Harmsen et al. | |
| 2002/0082498 A1 | 6/2002 | Wendt et al. | |
| 2002/0163482 A1 | 11/2002 | Sullivan | |
| 2002/0165594 A1 | 11/2002 | Biel | |
| 2003/0055307 A1 | 3/2003 | Elmaleh et al. | |
| 2003/0191379 A1 | 10/2003 | Benaron et al. | |
| 2004/0009341 A1* | 1/2004 | Naasani | B82Y 15/00 428/323 |
| 2004/0010192 A1 | 1/2004 | Benaron et al. | |
| 2004/0073120 A1 | 4/2004 | Motz et al. | |
| 2004/0225222 A1 | 11/2004 | Zeng et al. | |
| 2004/0254419 A1 | 12/2004 | Wang et al. | |
| 2004/0254454 A1 | 12/2004 | Kockro | |
| 2005/0014851 A1 | 1/2005 | Bringley | |
| 2005/0074779 A1 | 4/2005 | Vo-Dinh | |
| 2005/0143662 A1 | 6/2005 | Marchitto et al. | |
| 2005/0221494 A1 | 10/2005 | Natan | |
| 2005/0272160 A1 | 12/2005 | Natan | |
| 2005/0277816 A1 | 12/2005 | Maier et al. | |
| 2006/0008924 A1 | 1/2006 | Anker et al. | |
| 2006/0054506 A1 | 3/2006 | Natan et al. | |
| 2006/0098194 A1 | 5/2006 | Tuschel | |
| 2006/0173293 A1 | 8/2006 | Marquart et al. | |
| 2007/0010809 A1 | 1/2007 | Hovda et al. | |
| 2007/0134805 A1 | 6/2007 | Gilbert | |
| 2007/0167838 A1 | 7/2007 | Hubble et al. | |
| 2007/0178067 A1 | 8/2007 | Maier et al. | |
| 2007/0232874 A1 | 10/2007 | Ince | |
| 2007/0238953 A1 | 10/2007 | Lucassen et al. | |
| 2007/0255356 A1 | 11/2007 | Rose et al. | |
| 2007/0260295 A1 | 11/2007 | Chen et al. | |
| 2007/0269382 A1 | 11/2007 | Santra et al. | |
| 2007/0282190 A1 | 12/2007 | Dekel et al. | |
| 2008/0007716 A1 | 1/2008 | Igarashi | |
| 2008/0058908 A1 | 3/2008 | Bornstein | |
| 2008/0089839 A1 | 4/2008 | Lu et al. | |
| 2008/0095852 A1* | 4/2008 | Kong | A61K 9/5115 424/489 |
| 2008/0118912 A1 | 5/2008 | Dickson et al. | |
| 2008/0119832 A1 | 5/2008 | Cronin | |
| 2008/0305045 A1 | 12/2008 | Kuniyil et al. | |
| 2009/0137666 A1 | 5/2009 | Wang et al. | |
| 2009/0171330 A1 | 7/2009 | Taylor et al. | |
| 2009/0204111 A1 | 8/2009 | Bissig et al. | |
| 2009/0218550 A1 | 9/2009 | Koyakutty et al. | |
| 2009/0237648 A1 | 9/2009 | Armstrong et al. | |
| 2009/0263485 A1 | 10/2009 | Li et al. | |
| 2009/0281536 A1 | 11/2009 | Beckman et al. | |
| 2009/0285766 A1 | 11/2009 | Kishen et al. | |
| 2009/0294692 A1 | 12/2009 | Bourke, Jr. et al. | |
| 2009/0304581 A1 | 12/2009 | Scheinberg et al. | |
| 2010/0016783 A1 | 1/2010 | Bourke, Jr. et al. | |
| 2010/0045778 A1 | 2/2010 | Yelin | |
| 2010/0166650 A1 | 7/2010 | Gambhir | |
| 2010/0197937 A1 | 8/2010 | Minami et al. | |
| 2010/0211137 A1 | 8/2010 | Kim et al. | |
| 2010/0279272 A1 | 11/2010 | Burrell et al. | |
| 2010/0322471 A1 | 12/2010 | Treado et al. | |
| 2011/0020239 A1 | 1/2011 | Butte et al. | |
| 2011/0021970 A1* | 1/2011 | Vo-Dinh | A61K 49/0039 604/20 |
| 2011/0152692 A1 | 6/2011 | Nie et al. | |
| 2011/0165077 A1 | 7/2011 | Qian et al. | |
| 2011/0182881 A1 | 7/2011 | Chin et al. | |
| 2011/0190760 A1 | 8/2011 | Niver et al. | |
| 2011/0207231 A1 | 8/2011 | Natan et al. | |
| 2011/0230760 A1 | 9/2011 | Gambhir et al. | |
| 2011/0242533 A1 | 10/2011 | Treado et al. | |
| 2011/0261351 A1 | 10/2011 | Treado et al. | |
| 2011/0262351 A1 | 10/2011 | Chung et al. | |
| 2011/0263920 A1 | 10/2011 | Bourke, Jr. et al. | |
| 2011/0282181 A1 | 11/2011 | Wang et al. | |
| 2012/0123205 A1 | 5/2012 | Nie et al. | |
| 2012/0136241 A1 | 5/2012 | Chen et al. | |
| 2012/0141981 A1 | 6/2012 | Pantazis et al. | |
| 2012/0164624 A1 | 6/2012 | Natan et al. | |
| 2012/0179029 A1 | 7/2012 | Kircher et al. | |
| 2012/0212733 A1 | 8/2012 | Kodali et al. | |
| 2012/0226139 A1 | 9/2012 | Peyman | |
| 2012/0251450 A1 | 10/2012 | Punnoose et al. | |
| 2012/0282632 A1 | 11/2012 | Chiu et al. | |
| 2012/0283379 A1 | 11/2012 | Auger et al. | |
| 2012/0302940 A1 | 11/2012 | Ray | |
| 2013/0012794 A1 | 1/2013 | Zeng et al. | |
| 2013/0023770 A1 | 1/2013 | Courtney et al. | |
| 2013/0029360 A1 | 1/2013 | Suh et al. | |
| 2013/0040292 A1 | 2/2013 | Fernandez Lopez et al. | |
| 2013/0137944 A1 | 5/2013 | Jeong et al. | |
| 2013/0231573 A1 | 9/2013 | Zeng et al. | |
| 2013/0330839 A1 | 12/2013 | Suh et al. | |
| 2013/0342683 A1 | 12/2013 | Nelson et al. | |
| 2014/0140594 A1 | 5/2014 | Mahadevan-Jansen et al. | |
| 2014/0316255 A1 | 10/2014 | Garai et al. | |
| 2014/0350534 A1 | 11/2014 | Kircher et al. | |
| 2015/0018807 A1 | 1/2015 | Kircher et al. | |
| 2015/0182296 A1 | 7/2015 | Daon et al. | |
| 2015/0328346 A1 | 11/2015 | Harmsen et al. | |
| 2016/0000329 A1 | 1/2016 | Kircher et al. | |
| 2016/0000330 A1 | 1/2016 | Huang et al. | |
| 2016/0018404 A1 | 1/2016 | Iyer et al. | |
| 2016/0166194 A1 | 6/2016 | Gareau et al. | |
| 2017/0138860 A1 | 5/2017 | Huang | |
| 2017/0296293 A1 | 10/2017 | Mak et al. | |

FOREIGN PATENT DOCUMENTS

| | | |
|---|---|---|
| CN | 102770071 A | 11/2012 |
| CN | 102559190 B | 9/2013 |
| DE | 102 49 674 A1 | 5/2004 |
| DE | 10 2011 103 950 A1 | 12/2012 |
| JP | H09-005666 A | 1/1997 |
| JP | H11-084307 A | 3/1999 |
| JP | 2003/503135 A | 1/2003 |
| JP | 2004/193545 A | 7/2004 |
| JP | 2005 306827 A | 11/2005 |
| JP | 2009/011546 A | 1/2009 |
| JP | 2009/508571 A | 3/2009 |
| JP | 2009/511891 A | 3/2009 |
| JP | 2009/115546 A | 5/2009 |
| JP | 2009/222713 A | 10/2009 |
| JP | 2010/523983 A | 7/2010 |
| JP | 2011-158334 A | 8/2011 |
| TW | 572748 B | 1/2004 |
| WO | WO-90/03803 A1 | 4/1990 |
| WO | WO-93/03672 A1 | 3/1993 |
| WO | WO-00/41611 A2 | 7/2000 |
| WO | WO-01/01854 A2 | 1/2001 |
| WO | WO-02/100285 A1 | 12/2002 |
| WO | WO-2005/107623 A2 | 11/2005 |
| WO | WO-2008/122035 A1 | 10/2008 |
| WO | WO-2010/096828 A1 | 8/2010 |
| WO | WO-2010/111066 A2 | 9/2010 |
| WO | WO-2011/025640 A1 | 3/2011 |
| WO | WO-2011/084528 A1 | 7/2011 |
| WO | WO-2012/065163 A2 | 5/2012 |
| WO | WO-2014/036470 A1 | 3/2014 |
| WO | WO-2014/089247 A2 | 6/2014 |
| WO | WO-2014/100380 A2 | 6/2014 |
| WO | WO-2014/130736 A1 | 8/2014 |
| WO | WO-2016/028749 A1 | 2/2016 |

(56) References Cited

FOREIGN PATENT DOCUMENTS

| WO | WO-2016/149378 A1 | 9/2016 |
|---|---|---|
| WO | WO-2016/179260 A1 | 11/2016 |
| WO | WO-2018/213851 A1 | 11/2018 |

OTHER PUBLICATIONS

Written Opinion, PCT/US2015/045646, dated Nov. 27, 2015, 7 pages.

Debbage, P. and Jaschke, W., Molecular imaging with nanoparticles: giant roles for dwarf actors, Histochem. Cell Biol., 130(5):845-75 (2008).

Extended European Search Report for EP 13832980.0, 9 pages (dated Apr. 20, 2016).

Fales, A.M. et al., Silica-coated gold nanostars for combined surface-enhanced Raman scattering (SERS) detection and singlet-oxygen generation: a potential nanoplatform for theranostics, Langmuir, 27(19):12186-90 (2011).

Lusic, H. and Grinstaff, M.W., X-ray-computed tomography contrast agents, Chem. Rev., 113(3):1641-66 (2013).

Massoud, T.F. and Gambhir, S.S., Molecular imaging in living subjects: seeing fundamental biological processes in a new light, Genes Dev., 17(5):545-80 (2003).

Wieboldt, Dick, Understanding Raman Spectrometer Parameters, Spectroscopy, Special Issue, 6 pages (2010).

Harmsen, S. et al., Surface-enhanced resonance Raman scattering nanostars for high-precision cancer imaging, Science Translational Medicine, 7(271):1-8 (2015).

International Preliminary Report on Patentability, Application No. PCT/US13/57636, dated Aug. 1, 2014, 27 pages.

International Search Report, PCT/US13/57636, dated Jan. 3, 2014, 3 pages.

International Search Report, PCT/US13/76475, dated Jun. 16, 2014, 4 pages.

Kim, J. et al., Multifunctional nanostructured materials for multimodal imaging, and simultaneous imaging and therapy, Chem. Soc. Rev., 38:372-390 (2009).

Written Opinion, PCT/US13/57636, dated Jan. 3, 2014, 12 pages.

Written Opinion, PCT/US13/76475, dated Jun. 16, 2014, 8 pages.

Adiseshaiah, P.P. et al., Nanomaterial standards for efficacy and toxicity assessment, Advanced Review, 2:99-112 (2009).

Agarwal, A. et al., Targeted gold nanorod contrast agent for prostate cancer detection by photoacoustic imaging, Journal of Applied Physics, 102:064701-064704 (2007).

Aggarwal, S. et al., What's fueling the biotech engine—2009-2010, Nature Biotechnology, 28(11):1165-1171 (2010).

Beljebbar, A. et al., Ex vivo and in vivo diagnosis of C6 glioblastoma development by Raman spectroscopy coupled to a microprobe, Anal Bioanal Chem, 398:477-487 (2010).

Binkley, J. et al., RNA ligands to human nerve growth factor, Nucleic Acids Research, 23(16):3198-3205 (1995).

Bucci, M.K. et al., Near Complete Surgical Resection Predicts a Favorable Outcome in Pediatric Patients with Nonbrainstem, Malignant Gliomas, Cancer, 101(4): 817-824 (2004).

De La Zerda, A. et al., A Comparison Between Time Domain and Spectral Imaging Systems for Imaging Quantum Dots in Small Living Animals, Molecular Imaging and Biology, 12:500-508 (2010).

De La Zerda, A. et al., Advanced contrast nanoagents for photoacoustic molecular imaging, cytometry, blood test and photothermal theranostics, Contrast Media Mol. Imaging, 6:346-369 (2011).

De La Zerda, A. et al., Carbon nanotubes as photoacoustic molecular imaging agents in living mice, Letters, Nature Nanotechnology, 3:557-562 (2008).

De La Zerda, A. et al., Ultrahigh Sensitivity Carbon Nanotube Agents for Photoacoustic Molecular Imaging in Living Mice, Nano Letters, 10:2168-2172 (2010).

Eghtedari, M. et al., High Sensitivity of In Vivo Detection of Gold Nanorods Using a Laser Optoacoustic Imaging System, Nano Letters, 7(7):1914-1918 (2007).

Ermilov, S.A. et al., Laser optoacoustic imaging system for detection of breast cancer, Journal of Biomedical Optics, 14(2):024007-1-14 (2009).

Haaland, D.M. and Easterling, R.G., Improved Sensitivity of Infrared Spectroscopy by the Application of Least Squares Methods, Applied Spectroscopy, 34(5):539-548 (1980).

International Search Report, PCT/US2014/017508, dated May 12, 2014, 3 pages.

Jellinek, D.J. et al., Inhibition of Receptor Binding by High-Affinity RNA Ligands to Vascular Endothelial Growth Factor, Biochemistry, 33:10450-10456 (1994).

Kantelhardt, S.R. et al., Multiphoton Excitation Fluorescence Microscopy of 5-Aminolevulinic Acid Induced Fluorescence in Experimental Gliomas, Laser in Surgery and Medicine, 40:273-281 (2008).

Keren, S. et al., Noninvasive molecular imaging of small living subjects using Raman spectroscopy, PNAS, 105(15):5844-5849 (2008).

Kim, G. et al., Indocyanine-green-embedded PEBBLEs as a contrast agent of photoacoustic imaging, Journal of Biomedical Optics, 12(4):044020-1-8 (2007).

Kim, J. et al., Golden carbon nanotubes as multimodal photoacoustic and photothermal high-contrast molecular agents, Nature Nanotechnology, 4:688-694 (2009).

Kircher, M.F. et al., A brain tumor molecular imaging strategy using a new triple-modality MRI-photoacoustic-Raman nanoparticle, Nature Medicine, 18(5):829-834 (2012).

Kircher, M.F. et al., Noninvasive cell-tracking methods, Nature Reviews: Clinical Oncology, 8:677-688 (2011).

Knauth, M. et al., Low-field interventional MRI in neurosurgery: finding the right dose of contrast medium, Neuroradiology, 43:254-258 (2001).

Knauth, M. et al., Surgically Induced Intracranial Contrast Enhancement: Potential Source of Diagnostic Error in Intraoperative MR Imaging, AJNR Am J Neuroradiol, 20:1547-1553 (1999).

Koljenovic, S. et al., Raman Spectroscopic Characterization of Porcine Brain Tissue Using a Single Fiber-Optic Probe, Anal. Chem., 79:557-564 (2007).

Loening, A.M. And Gambhir, S.S., AMIDE: A Free Software Tool for Multimodality Medical Image Analysis, Molecular Imaging, 2(3):131-137 (2003).

Lüdemann, L. et al., Pharmacokinetic analysis of glioma compartments with dynamic Gd-DTPA-enhanced magnetic resonance imaging, Magnetic Resonance Imaging, 18:1201-1214 (2000).

Maeda, H. et al., Tumor vascular permeability and the EPR effect in macromolecular therapeutics: a review, Journal of Controlled Release, 65:271-284 (2000).

Mansfield, J.R. et al., Autofluorescence removal, multiplexing, and automated analysis methods for in-vivo fluorescence imaging, Journal of Biomedical Optics, 10(4):041207-1-9 (2005).

Mcnay, G. et al., Surface-Enhanced Raman Scattering (SERS) and Surface-Enhanced Resonance Raman Scattering (SERRS): A Review of Applications, Applied Spectroscopy, 65(8):825-837 (2011).

Ozawa, T. et al., Bromophenol Blue Staining of Tumors in a Rat Glioma Model, Neurosurgery, 57(4):1041-1047 (2005).

Pelletier, M.J., Quantitative Analysis Using Raman Spectrometry, 57(1):20A-42A (2003).

Razansky, D. et al., Multispectral opto-acoustic tomography of deep-seated fluorescent proteins in vivo, Nature Photonics, 3:412-417 (2009).

Reinges, M.H.T. et al., Course of brain shift during microsurgical resection of supratentorial cerebral lesions: limits of conventional neuronavigation, Acta Neurochir, 146:369-377 (2004).

Robbins, S.L. and Angell, M., Neoplasia and Other Disturbances of Cell Growth, Basic Pathology: Non-Neoplastic Cell Growth, 2(3):68-105 (1976).

Schneider, J.P. et al., Intraoperative MRI to guide the resection of primary supratentorial glioblastoma multiforme—a quantitative radiological analysis, Neuroradiology, 47:489-500 (2005).

Shinoda, J. et al., Fluorescence-guided resection of glioblastoma multiforme by using high-dose fluorescein sodium, J Neurosurg, 99:597-603 (2003).

(56) References Cited

OTHER PUBLICATIONS

Short, M.A. et al., Development and preliminary results of an endoscopic Raman probe for potential in vivo diagnosis of lung cancers, Optics Letters, 33(7):711-713 (2008).
Stewart et al., Raman Imaging, Annual Review of Analytical Chemistry, 5:337-360 (2012).
Stummer, W. et al., Fluorescence-guided surgery with 5-aminolevulinic acid for resection of malignant glioma: a randomised controlled multicentre phase III trial, Oncology: The Lancet, 7:392-401 (2006).
Stupp, R. et al., Changing Paradigms—An Update on the Multidisciplinary Management of Malignant Glioma, The Oncologist, 11:165-180 (2006).
Thakor, A.S. et al., Oxidative Stress Mediates the Effects of Raman-Active Gold Nanoparticles in Human Cells, Nanoparticle Cytotoxicity, 7(1):126-136 (2011).
Thakor, A.S. et al., The Fate and Toxicity of Raman-Active Silica-Gold Nanoparticles in Mice, Drug Delivery, Science Translation Medicine, 3(79):1-11 (2011).
Toms, S.A. et al., Intraoperative Optical Spectroscopy Identifies Infiltrating Glioma Margins with High Sensitivity, Operative Neurosurgery, 57(4):382-391 (2005).
Tréhin, R. et al., Fluorescent Nanoparticle Uptake for Brain Tumore Visualization, Neoplasia, 8(4):302-311 (2006).
Tuerk, C. and MacDougal-Waugh, S., In vitro evolution of functional nucleic acids: high-affinity RNA ligands of HIV-1 proteins, Gene, 137:33-39 (1993).
Wang, L.V., Multiscale photoacoustic microscopy and computed tomography, Nature Photonics, 3:503-209 (2009).
Written Opinion, PCT/US2014/017508, dated May 12, 2014, 12 pages.
Yigit, M.V. and Medarova, Z., In vivo and ex vivo applications of gold nanoparticles for biomedical SERS imaging, Am J Nucl Med Mol Imaging, 2(2):232-341 (2012).
Zavaleta, C. et al., Noninvasive Raman Spectroscopy in Living Mice for Evaluation of Tumor Targeting with Carbon Nanotubes, Nano Letters, 8(9):2800-2805 (2008).
Zavaleta, C.L. et al., Multiplexed imaging of surface enhanced Raman scattering nanotags in living mice using noninvasive Raman spectroscopy, PNAS, 106(32):13511-13516 (2009).
Zavaleta, C.L. et al., Preclinical Evaluation of Raman Nanoparticle Biodistribution for their Potential Use in Clinical Endoscopy Imaging, Small, 7(15):2232-2240 (2011).
Zavaleta, C.L. et al., Raman's "Effect" on Molecular Imaging, J Nucl Med., 52:1839-1844 (2011).
Zhang, Y. et al., Molecular Imaging with SERS-Active Nanoparticles, Small, 7(23):3261-3269 (2011).
Harmsen, S. et al., Rational design of a chalcogenopyrylium-based surface-enhanced resonance Raman scattering nanoprobe with attomolar sensitivity, Nature Communications, 6:6570 | DOI: 10.1038/ncomms7570, pp. 1-9, Additional Information added, 8 pages.
Huang, J. et al., Preparation of Silica-Encapsulated Hollow Gold Nanosphere Tags Using Layer-by-Layer Method for Multiplex Surface-Enhanced Raman Scattering Detection, Langmuir, 27:10228-10233 (2011).
Huang, R. et al., High Precision Imaging of Microscopic Spread of Blioblastoma with a Targeted Ultrasensitive SERRS Molecular Imaging Probe, Theranostics, 6(8):1075-1084 (2016).
Huang, X. et al., Gold nanoparticles: interesting optical properties and recent applications in cancer diagnostics and therapy, Nanomedicine, 2(5):681-693 (2007).

Kaaki, K. et al., Magnetic Nanocarriers of Doxorubicin Coated with Poly(ethylene glycol) and Folic Acid: Relation between Coating Structure, Surface Properties, Colloidal Stability, and Cancer Cell Targeting, Langmuir, 28:1496-1505 (2012).
Kim, K. et al., Silver-Coated Dye-Embedded Silica Beads: A Core Material of Dual Tagging Sensors Based on Fluorescence and Raman Scattering, ACS Applied Materials & Interfaces, 3:324-330 (2011).
Kim, K. et al., Silver-particle-based surface-enhanced resonance Raman scattering spectroscopy for biomolecular sensing and recognition, Anal Bioanal Chem., 388:81-88 (2007).
Kodali, A., et al., Optimally designed nanolayered metal-dielectric particles as probes for massively multiplexed and ultrasensitive molecular assays, PNAS, 107(31)13620-13625 (2010).
Qian, X. et al., In vivo tumor targeting and spectroscopic detection with surface-enhanced Raman nanoparticle tags, Nature Biotechnology, 26(1):83-90, (2008).
Shona, S. et al., Raman Imaging, Annu. Rev. Anal. Chem. 5:337-360 (2012).
Supplementary Partial European Search Report, European International Application No. 14753802.9, 8 pages, dated Oct. 20, 2016.
Tognalli, N. et al., From Single to Multiple Ag-Layer Modification of Au Nanocavity Substrates: A Tunable Probe of the Chemical Surface-Enhanced Raman Scattering Mechanism, ACS Nano, 5(7):5433-5443 (2011).
Declaration of Moritz Kircher for U.S. Appl. No. 14/464,642, 16 pages, executed Dec. 5, 2016.
Esenturk, E. N. and Walker, A. R. H., Surface-enhanced Raman scattering spectroscopy via gold nanostars, Journal of Raman Spectroscopy, 40(1): 86-91 (2009).
International Search Report for PCT/US2015/042441, 3 pages (dated Oct. 19, 2015).
Written Opinion for PCT/US2015/042441, 16 pages (dated Oct. 19, 2015).
Yi, Z. et al, Facile preparation of Au/Ag bimetallic hollow nanospheres and its application in surface-enhanced Raman scattering, Applied Surface Science, 258(1): 212-217 (2011).
Yigit, M. V. et al, Noninvasive MRI-SERS Imaging in Living Mice Using an Innately Bimodal Nanomaterial, ACS NANO, 5(2): 1056-1066 (2011).
Yuan, H. et al., Quantitative Surface-Enhanced Resonant Raman Scattering Multiplexing of Biocompatible Gold Nanostars for in Vitro and ex Vivo Detection, Analytical Chemistry, 85:208-212 (2012).
Zong, S. et al., A SERS and fluorescence dual mode cancer cell targeting probe based on silica coated Au@Ag core-shell nanorods, Talanta, 97:368-375 (2012).
Cheng, F. et al, Chelator-Free Synthesis of a Dual-Modality PET/MRI Agent, Angew. Chem. Int. Ed., 52: 13319-13323 (2013).
Lee, S. B. et al, Mesoporous Silica Nanoparticle Pretargeting for PET Imaging Based on a Rapid Bioorthogonal Reaction in a Living Body, Angew. Chem. Int. Ed., 52: 10549-10552 (2013).
Sun, X. et al, Self-Illuminating $^{64}$Cu-Doped CdSe/ZnS Nanocrystals in Vivo Tumor Imaging, Journal of the American Chemical Society, 136: 1706-1709 (2014).
Sá, L. T. M. et al, Development of Nanoaptamers Using a Mesoporous Silica Model Labeled with $^{99m}$Tc for Cancer Targeting, Oncology, 82: 213-217 (2012).
Von Maltzahn et al., SERS-Coded Gold Nanorods as a Multifuntional Platform for Densely Multiplexed Near-Infrared Imaging and Photothermal Heating, Advanced Material, 21:3175-3180 (2009).

* cited by examiner

|  | Sensitivity | Signal Specificity | Resolution | Speed | Depth | 3D |
|---|---|---|---|---|---|---|
| MPR-Raman | +++++ | +++++ | +++++ | +++ | + | No |
| MPR-PAT | ++++ | ++++ | ++++ | +++++ | ++ | Yes |
| MPR-MRI | +++ | ++ | ++ | + | +++++ | Yes |
| Gd-MRI | + | + | ++ | + | +++++ | Yes |
| Fluorescence | +++ | +++ | +++++ | +++++ | + | No |
| PET | ++++ | +++++ | + | +++ | +++++ | Yes |
| CT | + | + | +++ | +++++ | +++++ | Yes |
| Ultrasound | + | + | ++++ | +++++ | +++ | Yes |

+ = weakest     +++++ = strongest

Figure 29

PARTICLES, METHODS AND USES THEREOF

CROSS-REFERENCE TO RELATED APPLICATIONS

This application is a 35 U.S.C. 371 National Stage of International Patent Application No. PCT/US2013/57636, filed Aug. 30, 2013, which designated the U.S. and which claims priority to and the benefit of, U.S. Provisional Patent Application No. 61/696,122, filed Aug. 31, 2012, the contents of each of which are entirely incorporated herein by reference.

GOVERNMENT SUPPORT

This invention was made with government support under grant numbers CA008748 and CA163961 awarded by the National Institutes of Health. The government has certain rights in the invention.

BACKGROUND

Nanoparticle systems that can incorporate dopant entities have tremendous potential and are useful in a wide variety of contexts. There is a continuing need for improved systems. One particular goal in developing such systems is to provide imaging nanoparticles that can be utilized in surgery to define resection boundaries. Completeness of surgical resection profoundly impacts morbidity and mortality. The challenges and significance are particularly acute in surgery to remove tumors. In trying to achieve more complete tumor resections, the surgeon encounters several hurdles, which include irregular and indistinct tumor margins as well as tumor growth adjacent to or invading crucial physiological structures. A wide variety of techniques have been explored to date in an effort to better visualize tumor margins. However, there remains a continuing need for new and better probes and/or methods. In particular, there is an important, unmet need for a real-time probe/method for accurately detecting residual tumor.

SUMMARY

The present invention provides technologies relevant to particles (e.g., surface-enhanced (resonance) Raman scattering (SE(R)RS)-active particles), including technologies for preparing particles, and/or for using particles, as well as particles themselves. In general, particles as described and/or utilized herein contain a nanoscale core, an encapsulant, and a plurality of dopant entities.

Provided compositions and methods are useful in a variety of contexts. To give but one example, in many embodiments, the present invention is particularly useful for particles wherein dopant entities are resonant agents, which experience resonance at an incident laser wavelength. In certain embodiments, a resonant agent is a SE(R)RS-active agent. As demonstrated herein, provided technologies achieve unprecedented levels of dopant entity density and/or surface localization, which, for a SE(R)RS-active agent dopant, results in dramatically improved signal intensity and/or imaging sensitivity.

Among other things, the invention provides technologies that permit an encapsulant coating without use of a surface primer. Such a surface primer is often added to enable encapsulant binding to the nanoscale core surface. In some embodiments, the invention provides technologies that utilize a displaceable capping entity. Features of provided technologies include a higher density of dopant entities can be located close to its core surface. More traditional approaches that utilize a surface primer do not permit such a degree of density and/or surface localization of dopant entities.

In some embodiments, methodologies described herein include steps of providing a nanoscale core in association with a capping agent (e.g., surface-bound stabilizing agent present as a direct consequence of the nanoscale core synthesis); contacting the capping-agent associated nanoscale core with an encapsulant precursor and a dopant entity under conditions and for a time sufficient for the encapsulant precursor and/or dopant entity to displace some or all of the capping agent to produce a particle characterized by high density of surface-localized doping entity.

Provided technologies permit preparation of particles of previously unachieved structure and properties. In some embodiments, provided particles include a nanoscale core, an encapsulant, and a plurality of dopant entities, which particles are characterized by: (i) dopant entity density higher than typically observed for the relevant dopant entity; and (ii) localization of the dopant entity closer to the nanoscale core than typically observed.

One remarkable feature of provided technologies for preparing particles is that they are applicable to and effective with a wide range of core materials, core configurations, encapsulant and entity materials, etc. In some embodiments, provided particles comprise a core of a metal material (e.g., gold, silver, copper, etc.). In some embodiments, provided particles comprise a nanoscale core, whose shape is or includes structural elements selected from the group consisting of spheres, rods, stars, shells, ellipses, triangles, pyramids, cubes, cages and combinations thereof. In some particular embodiments, provided particles include a nanoscale core having a central structure surrounded by satellite structures.

The present disclosure, among other things, provides compositions that include a nanoscale core; a plurality of capping agent entities associated on the core; an outer encapsulant layer; and a plurality of dopant entities distributed at locations selected from the group consisting of: on or within the nanoscale core, on or between capping agent entities, on or within the encapsulating layer, and combinations thereof. Provided technologies can achieve unprecedented levels of dopant entity density and/or surface localization, which, in some embodiments, including for example in certain embodiments that utilize one or more SE(R)RS-active agent dopant(s), results in dramatically improved signal intensity and/or imaging sensitivity. In some embodiments, signal intensity and/or imaging sensitivity is improved relative to is improved relative to known imaging modalities, including CT, Ultrasound, or Fluorescence.

The present disclosure provides, among other things, methods of applying an encapsulant layer to a nanoscale core. In some embodiments, provided methods include steps of providing a capped composition including a nanoscale core substantially coated with a plurality of capping agent entities displaceably associated with the nanoscale core's surface. Alternatively or additionally, in some embodiments, provided methods include steps of contacting a capped composition with a plurality of dopant entities and a plurality of encapsulant precursor entities, the contacting being performed under conditions and for a time sufficient to permit i) accumulation of dopant entities onto or nearby the core surface; and ii) formation of an outer encapsulant layer by the encapsulant precursor entities such that a composition is generated that includes a nanoscale core; a plurality of capping agent entities associated on the core; an outer encapsulant layer; and a plurality of dopant entities distributed at locations selected from the group consisting of: on or within the core, on capping agent entities, within the encapsulating layer, on the encapsulating layer and combinations thereof.

The present disclosure, provides, among other things, methods including steps of administering to a subject a collection of particles including a nanoscale core; a plurality of capping agent entities associated on the core; an outer encapsulant layer; and a plurality of dopant entities distributed at locations selected from the group consisting of: on or within the nanoscale core, on capping agent entities, within the encapsulating layer, on the encapsulating layer and combinations thereof. In certain embodiments, such particles further include MRI agents, PET agents, SPECT agents, CT agents and/or combination thereof. In certain embodiments, such methods also include one or more steps of imaging localized particles. In certain embodiments, a step of imaging localized particles includes obtaining a first signal selected from the group consisting of MRI signals, PET signals, SPECT signals, CT signals, and combinations thereof, wherein the first signal is used to produce an image corresponding to one or more of: tumor localization (e.g., of a whole tumor), macroscopic delineation of a tumor (e.g., of a whole tumor), and/or location, shape, and/or size of residual tumor; obtaining a photoacoustic signal, wherein the photoacoustic signal is used to produce an image corresponding to a tumor with deep tissue penetration; obtaining a Raman vibrational signal, wherein the Raman vibrational signal is used as a guide to define tumor margins; and producing an image of a tumor and its margins using the first signal, the photoacoustic signal, and the Raman vibrational signal.

Definitions

In order for the present disclosure to be more readily understood, certain terms are defined below. Additional definitions for the following terms and other terms may be set forth throughout the specification, or may otherwise be clear from context.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In some embodiments, a route of administration is oral administration. Additionally or alternatively, a route is intravenous administration. However, any route of administration, such as topical, subcutaneous, peritoneal, intraarterial, inhalation, vaginal, rectal, nasal, introduction into the cerebrospinal fluid, or instillation into body compartments can be used.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Illuminating": The term "illuminating" as used herein refers to the application of a light source, including near-infrared (NIR), visible light, including laser light capable of exciting molecules and/or nanoscale cores of the embodiments of the particles herein disclosed.

"Magnetic Resonance Imaging": The term "magnetic resonance imaging (MRI)" as used herein refers to a medical imaging technique most commonly used in radiology to visualize the structure and function of the body. It provides detailed images of the body in any plane. MRI uses no ionizing radiation, but uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a subject lies in a scanner, the hydrogen nuclei (i.e., protons) found in abundance in an animal body in water molecules, align with the strong main magnetic field. A second electromagnetic field that oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different tissues of the body (e.g., fat versus muscle) realign at different speeds, the different structures of the body can be revealed. Contrast agents may be injected intravenously to enhance the appearance of blood vessels, tumors or inflammation. MRI is used to image every part of the body, but is particularly useful in neurological conditions, disorders of the muscles and joints, for evaluating tumors and showing abnormalities in the heart and blood vessels.

"Sample": The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

BRIEF DESCRIPTION OF THE DRAWING

The Drawing, which is comprised of at least the following Figures, is for illustration purposes only, not for limitation.

FIG. 6A shows images of a different mouse with liposarcoma, multiple small foci of Raman signal (1, 2, 3, 4, and 5) were found in the resection bed, after the bulk tumor had been resected by a surgeon.

FIG. 29 illustrates certain strengths and weaknesses of different imaging modalities. The strengths of three imaging modalities incorporated in MPR-Nanostars (top three rows) are highly complementary to each other.

DETAILED DESCRIPTION OF CERTAIN EMBODIMENTS

Embodiments of the present disclosure provide for particles, methods of making particles, methods of using particles and the like.

Various embodiments of the present invention employ surface-enhanced (resonance) Raman scattering (SE(R)RS). The enhancement of a (resonance) Raman signal is the result of multiplicative effects of at least two phenomena, (resonance) Raman scattering ((R)RS) and surface-enhanced Raman scattering (SERS).

Without wishing to be bound to any particular theory, particles described in some embodiments exhibit markedly improved Raman signals, than any that have been reported, resulting from one or more of the following parameters A) electromagnetic enhancement; B) chemical enhancement; C) dye resonance (e.g., a SE(R)RS-active agent is in resonance with an exciting laser wavelength). In some embodiments, such particles are particularly useful for in vivo imaging applications.

Particles

Particles used in accordance with the present disclosure, in theory, can be of any shape or design. In some embodiments, a particle can be or can comprise a sphere. Additionally or alternatively, a particle can be or can comprise a star, a rod, a cube, a rectangle, a cone, a pyramid, a cylinder, a tube, a ring, a tetrahedron, a hexagon, a octagon, a cage, or any irregular shapes.

In some embodiments, the greatest dimension or at least one dimension of a particle may be about or less than 10 µm, 5 µm, 1 µm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, the greatest dimension or at least one dimension of a particle may be more than 10 µm, 5 µm, 1 µm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, the greatest dimension or at least one dimension of a particle may be in a range of about 1 µm to about 5 nm. In some embodiments, the greatest dimension or at least one dimension of a particle may be in a range of about 300 nm to about 5 nm. In some embodiments, the greatest dimension or at least one dimension of a particle may be in a range of any two values above. In some embodiments, the dimension of a particle is a diameter, wherein the diameter can be in a range as mentioned above. In some embodiments, the dimensions of a particle can be represented by a length, a width or a height in X, Y and Z axis, wherein each dimension can be in a range as mentioned above.

In certain embodiments, particle sizes and surface charges are tuned to enter tumors due to their leaky vasculature and are retained mostly via phagocytosis by tumor (associated) cells (known as "enhanced permeability and retention (EPR)" effect). In certain embodiments, particles do not wash out of a tumor, but are retained stably within the tumor (e.g., retention time at least 7 days).

Figure 1:
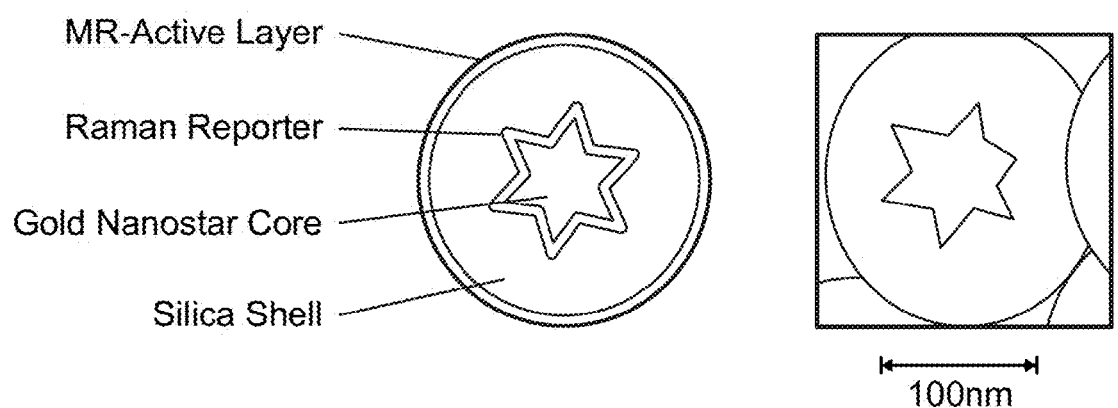
FIG. 1 shows a schematic of a SE(R)RS particle in accordance with the present invention together with a transmission electron micrograph (TEM) of a representative SE(R)RS particle. At the center of the SE(R)RS particle is a gold nanostar core coated with a layer of (resonance) Raman-active molecules (reporters). The star shape enables tuning of the Localized Surface Plasmon Resonance (LSPR) towards the Near-Infrared window and incorporates several "hot-spots" (the tips) of incredibly concentrated electric fields focused on the (resonance) Raman reporters. A shell of silica encapsulates this core, simultaneously protecting the (resonance) Raman reporters, preventing reactions of the core and reporters with the environment, and providing a surface for further functionalization. In this case, an MR-active layer is bound to the outer surface of the silica.

An exemplary particle suitable for use in accordance with the present disclosure is illustrated in FIG. 1. A particle may have an approximately spherical shape. Such a particle may have a diameter of approximately 50-300 nm.

In various embodiments, a particle described herein can comprise a nanoscale core, an encapsulant and one or more dopant entities. Referring to FIG. 1 (left), in certain embodiments, a nanoscale core is a gold nanostar, an encapsulant is silica and a dopant entity is a (resonance) Raman reporter and, in addition, an agent is an MRI agent. Such a particle may employ both surface-enhanced resonance Raman scattering (SE(R)RS) and MR capabilities and/or positron emission tomography (PET), single photon emission tomography (SPECT), computed tomography (CT), or Ultrasound (US) capabilities.

Nanoscale Core

A nanoscale core of a particle used in some embodiments of the present invention can be or can contain any metal or any other material capable of generating localized surface plasmon resonances (LSPRs).

In many embodiments, a metal is a SE(R)RS active metal. Such a metal can be any (metallic) substance capable of sustaining a (localized) surface plasmon resonance. In some embodiments, a SE(R)RS active metal is or comprises Au, Ag, Cu, Na, K, Cr, Al, or Li. A nanoscale core can also contain alloys of metals. In some embodiments, a nanoscale core is or contains Au, Ag or a combination thereof. In certain embodiments, a nanoscale core can provide a detectable photoacoustic signal.

A nanoscale core can be of any shape or design, and may contain one or more structural elements. In some embodiments, a nanoscale or at least one structural element of it is spherical. In some embodiments, a nanoscale core or at least one structural element of it is non-spherical. In some embodiments, a nanoscale core has structural elements selected from the group consisting of spheres, rods, stars, shells, ellipses, triangles, cubes, cages, pyramids and any combination thereof. For example, a nanoscale core can consist of or can comprise a star overlaid with at least one shell. To give another example, a nanoscale core can consist of or can comprise two or more concentric shells. In some particular embodiments, a nanoscale core can consist of or can comprise a central structure surrounded by satellite structures. Exemplary particles with various configurations are illustrated in FIGS. 15-18.

In some embodiments, a nanoscale core comprises at least two structural elements, separated from one another within a distance suitable for a plasmon hybridization effect. A distance can be an average distance. In certain embodiments, a distance between two separated structural elements is less than 100 nm, 50 nm, 30 nm, 20 nm, 15 nm, 10 nm, 8 nm, 5 nm or 3 nm, or 1 nm. In certain embodiments, a distance between two separated structural elements is in a range of about 100 nm to about 50 nm, about 50 nm to about 30 nm, about 30 nm to about 1 nm, or any two values above. In certain embodiments, individual structural elements are separated from one another or filled by an encapsulant.

In some embodiments, a nanoscale core is star-shaped. As used herein, the term "star shaped" refers to a body portion from which a plurality of protrusions extend. In some embodiments, a star shape is a true star shape. A "true star shape", as that term is used herein, comprises a body portion from which a plurality of protrusions extend radially. In some embodiments, a true star shape has at least one access of symmetry. In some embodiments, a true star shape is substantially symmetrical. In some embodiments, protrusions in a true star shape have approximately the same length. In some embodiments, protrusions have approximately the same width. In some embodiments, protrusions have substantially identical structures. In some embodiments, a true star shape has a body portion that is substantially spherical. In some embodiments, a true star shape has a body portion that is substantially rectangular or square. In some embodiments, protrusions substantially cover the body surface. In some embodiments, protrusions are configured on the body surface for high polarizabilities, for example so that intense localized surface plasmons can arise. It is contemplated that when a particle contains radially-protruding spikes, the coordinated electron oscillation becomes corralled into narrow regions (i.e., the tips) resulting in the build-up of a lot of charge in a very small region. Thus, a certain number of spikes results in an electromagnetic enhancement over a geometry which does not contain any. Nanoscale cores with an excess of spikes or asymmetric features, on the other hand, have smaller polarizabilities and cannot sustain large surface plasmon resonances because they encounter strong damping from the significant increase in electron-electron collisions, making coordinated oscillations of electrons weak and short-lived. FIG. 1 illustrates an example of a star-shaped nanoscale core.

In some embodiments, the greatest dimension or at least one dimension of a nanoscale core or its each component may be about or less than 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm or 1 nm. In some embodiments, the greatest dimension or at least one dimension of a nanoscale core or its each component may be more than 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm or 1 nm. In some embodiments, the greatest dimension or at least one dimension of a nanoscale core or its each component may be in a range of about 500 nm to about 5 nm or about 150 nm to about 5 nm. In some embodiments, the greatest dimension or at least one dimension of a nanoscale core or its each component may be in a range of about 100 nm to about 90 nm, about 90 nm to about 80 nm, about 80 nm to about 70 nm, about 70 nm to about 60 nm, about 60 nm to about 50 nm, about 50 nm to about 40 nm, about 40 nm to about 30 nm, about 30 nm to about 20 nm, about 20 nm to about 10 nm, about 10 nm to about 5 nm. In some embodiments, the greatest dimension or at least one dimension of a nanoscale core or its each component may be in a range of any two values above.

A nanoscale core with a desired size can be grown as metal colloids by a number of techniques well known in the art. For example, chemical or photochemical reduction of metal ions in solution using any number of reducing agents has been described. Likewise, syntheses of nanoscale cores can be carried out in constrained volumes, e.g. inside a vesicle. Nanoscale cores can also be made via electrical discharge in solution. Nanoscale cores can also be made by irradiating a metal with a high intensity pulsed laser. Example 1 demonstrates, in certain embodiments, a metal nanoscale core can be made via reduction with citrate or ascorbic acid, and hydrogen peroxide Encapsulant Particles provided by the present invention may include an encapsulant. In some embodiments, the encapsulant will substantially cover the particle's surface.

According to various embodiments of the present disclosure, an encapsulant can be or can comprise oxides including silica ($SiO_2$), titania ($TiO_2$), alumina ($Al_2O_3$), zirconia ($ZrO_2$), Germaniumdioxide (GeO2), etc., and non-oxides including pure metals or metal borides, carbides and nitrides, such as titanium and its combinations (Ti, $TiB_2$, TiC, TiN, etc.). Additionally or alternatively, metal (e.g., gold, silver, and the like) different from the core material, polymers including PEG and PLGA/PEG, and polymeric chelators (e.g., poly DOTA, dendrimer backbone, poly DTPA, or dendrimer alone), (multiwalled) carbon nanotubes, graphene, silicene.

An encapsulant in some embodiments is or comprises a dielectric. For example, an encapsulant such as silica can serve as a dielectric.

In some embodiments, an encapsulant is or includes silica. For example, a silica encapsulant can be synthesized from a silica precursor including, but not limited to, sodium silicate, alkylalkoxysilane; ethylpolysilicate; tetraethylorthosilicate (TEOS); tetramethylorthosilicate (TMOS); partially hydrolyzed TEOS; partially hydrolyzed TMOS or a combination thereof.

In some embodiments, an encapsulant is or includes one or more polymers, particularly polymers that which have been approved for use in humans by the U.S. Food and Drug Administration (FDA) under 21 C.F.R. § 177.2600, including, but not limited to, polyesters (e.g. polylactic acid, poly(lactic-co-glycolic acid), polycaprolactone, polyvalerolactone, poly(1,3-dioxan-2-one)); polyanhydrides (e.g. poly (sebacic anhydride)); polyethers (e.g., polyethylene glycol); polyurethanes; polymethacrylates; polyacrylates; polycyanoacrylates; copolymers of PEG and poly(ethylene oxide) (PEO).

In some embodiments, an encapsulant is or includes at least one degradable polymer. Such a degradable polymer can be hydrolytically degradable, biodegradable, thermally degradable, enzymatically degradable, and/or photolytically degradable polyelectrolytes. In some embodiments, degradation may enable release of one or more dopant entities (e.g., agent for delivery) associated with a particle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

An encapsulant layer on a nanoscale core can have an average thickness in various ranges. In some embodiments, an average thickness is about or less than 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, an averaged thickness is about or greater than 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, an averaged thickness is in a range from about 0.1 to about 200 nm, about 5 to about 50 nm or about 10 to about 30 nm. In some embodiments, an average thickness is in a range of any two values above.

In many embodiments of the present disclosure, an encapsulant can have or be modified to have one or more functional groups. Such functional groups (within or on the surface of an encapsulant layer) can be used for association with any agent (e.g., MRI agent, positron emission tomography (PET) tracer, single photon emission tomography (SPECT) tracer, fluorochrome, computed tomography (CT) agent, ultrasound (US) agent, targeting entity, or PEG).

Dopant Entity

Any entity of interest can be utilized as a dopant entity in accordance with the present invention. In some embodiments, dopant entities have sufficient affinity for one or more components of a particle to permit displacement of a capping agent and/or to permit high density and/or close surface localized loading of the dopant entity(ies) into or onto the particle.

In some embodiments, a dopant entity is or comprises a detectable entity. In some embodiments, a dopant entity is or comprises a dye, for example, a resonance dye. In some embodiments, a dopant entity is or comprises an agent useful in Raman spectroscopy. Exemplary dopant entities includes, but are not limited to, those agents described in the art such as in U.S. Pat. Nos. 5,306,403, 6,002,471, and 6,174,677, the contents of each of which is incorporated herein by reference in its entirety.

Figure 25:
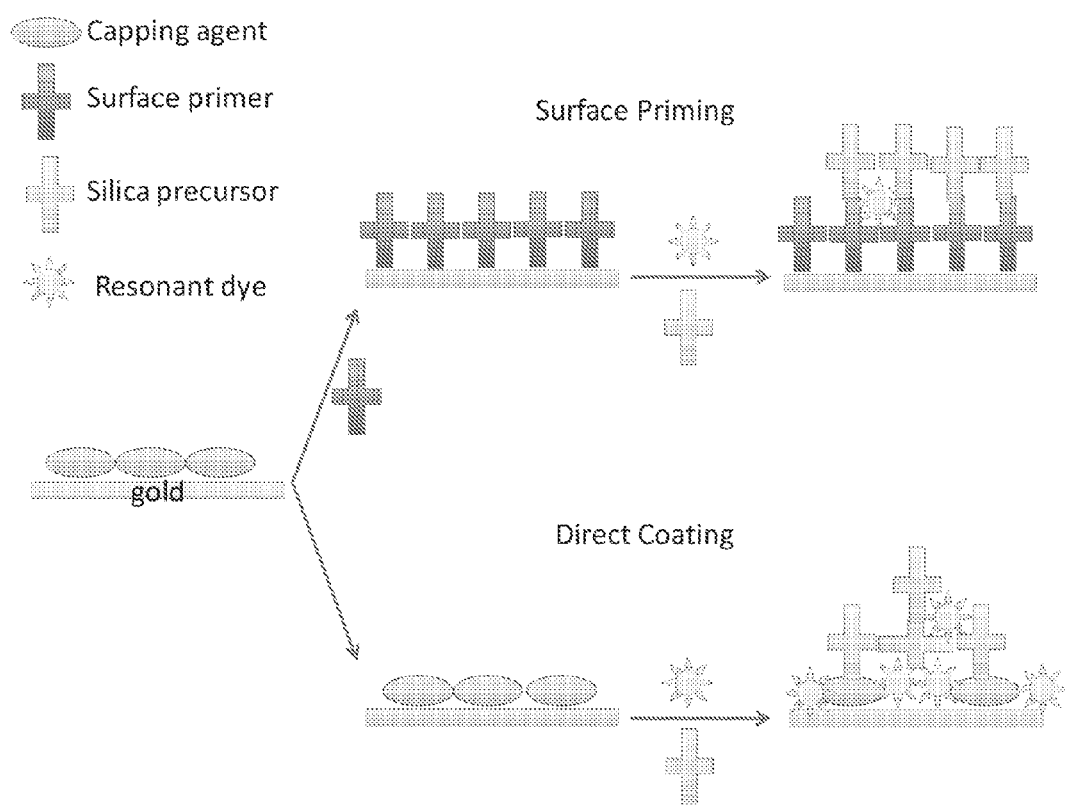
FIG. 25 illustrates methodologies for associating dopant entities on a particle surface with or without surface priming. In the top figure, a surface primer (e.g. 3-mercaptotrimethoxysilane, PEG-thiol, etc.) replaces the capping agent and in this way it provides stabilization to a particle, but more importantly it renders the surface vitreophilic (it acts as a primer for encapsulant to grow on). Since a surface primer has a greater affinity for the surface than a capping agent, the propensity of a dopant entity (e.g., a (resonance) Raman agent) to directly interact with the surface is decreased. In the bottom figure, we illustrate a method in which a capping agent is used stead of a surface primer. Since a capping agent interacts less strongly with the surface, the propensity of a dopant entity (e.g., a (resonance) Raman agent) to interact with the surface increases. Consequently, because the overall intensity of SE(R)RS signal generated by a particle depends on the number of (resonance) Raman reporter molecules near the particle surface, the signal is markedly enhanced.
Figure 26:
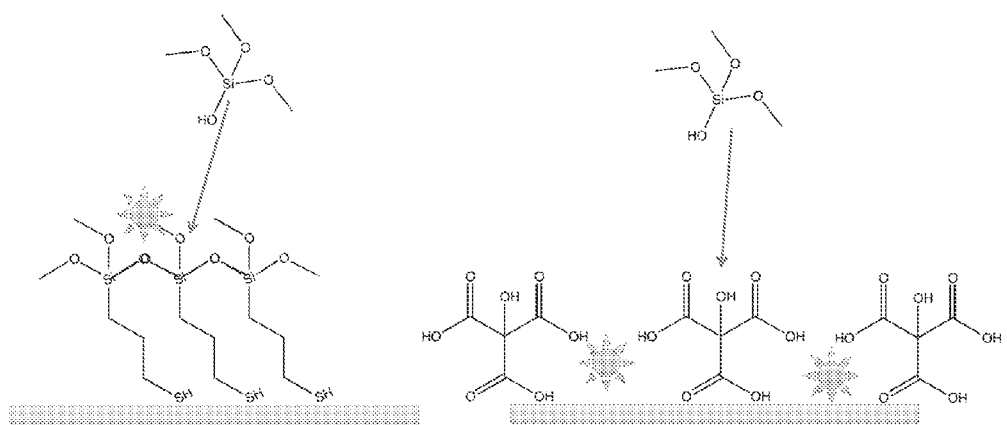
FIG. 26 illustrates two examples of the methods described herein. One uses a silica-based surface primer (left); the other uses citrate or ascorbate as a capping agent. A partially hydrolyzed TEOS is used as an exemplary precursor of a silica encapsulant.

In accordance with the present disclosure, dopant entities can be located on a nanoscale core (e.g., in direct contact with the surface of a nanoscale core), within a nanoscale core (e.g., in between structural elements of a nanoscale core), on or between capping agent entities, on or within an encapsulating layer, and any combination thereof. Some embodiments are illustrated in FIG. 25.

In some embodiments, at least some of a plurality of dopant entities are positioned within a short distance from the surface of a nanoscale core. Such a distance in various embodiments can be about or less than 1 nm, 2 nm, 3 nm, 4 nm, 5 nm, 6 nm, 7 nm, 8 nm, 9 nm, 10 nm, 15 nm, 20 nm. In some embodiments, a distance between a dopant entity and the surface of a nanoscale core is in a range of 2 nm to 5 nm, 5 nm to 10 nm, or 10 nm or 15 nm. In some embodiments, at least some of a plurality of dopant entities can be in direct contact with the surface of a nanoscale core.

In some particular embodiments, a dopant entity is a SE(R)RS-active agent. In some such embodiments, a high density of a SE(R)RS-active agent located close to a nanoscale core contributes to unprecedented Raman sensitivity achieved by a particle described herein. SE(R)RS-active agents generally benefit from signal intensity enhancement in the proximity of a metal surface. In accordance with the present disclosure, a skilled artisan in the art would be capable to choose a SE(R)RS-active agent, to achieve chemical enhancement and/or electromagnetic enhancement, considering factors such as core materials, core configurations, encapsulant material, etc. Such a SE(R)RS-active agent can have a charge transfer effect, from a metal to the molecule, or from the molecule to the metal.

A SE(R)RS-active agent refers to a molecule that is capable of generating a SERS or SE(R)RS spectrum when appropriately illuminated. Non-limiting examples of SE(R)RS-active agents include phthalocyanines such as methyl, nitrosyl, sulphonyl and amino phthalocyanines, naphthalocyanines, chalcogen-based dyes, azomethines, cyanines, squaraines, and xanthines such as the methyl, nitro, sulphano and amino derivatives. Each of these may be substituted in any conventional manner, giving rise to a large number of useful labels. It is noted that the choice of a SE(R)RS-active agent can be influenced by factors such as the resonance frequency of the molecule, the resonance frequency of other molecules present in a sample, etc.

Typically, detecting a SE(R)RS signal involves using incident light from a laser. The exact frequency chosen will depend on the SE(R)RS-active agent and on the metal surface (e.g., on the composition of the metal surface). Frequencies in visible or near-infrared spectrum tend, as a whole, to give rise to better surface enhancement effects for noble metal surfaces—such as those including silver and/or gold. However, it is possible to envisage situations in which other frequencies, for instance in the ultraviolet range, might be used. The selection and, if necessary, tuning of an appropriate light source, with an appropriate frequency and power, will be well within the capabilities of one of ordinary skill in the art, particularly with reference to available SE(R)RS literature.

The Raman enhancement generally is proportional to the density of a SE(R)RS-active agent associated (e.g., adsorbed) on a metal surface. A surprisingly high density of a SE(R)RS-active agent adsorbed on a core surface in accordance with the present disclosure may contribute to the superior sensitivity of particles disclosed herein.

Capping Agent

In some embodiments, a capping agent is an entity that can be or is displaceably associated with a nanoscale core. Without wishing to be bound by any particular theory, it is noted here that, in some embodiments, capping agents can play an important role in nanoscale core synthesis. In some embodiments, capping agent may control the size and geometry of a nanoscale core. In some embodiments, capping agents are present after synthesis as an adsorbed monolayer on the synthesized nanoscale core. In some embodiments, capping agents are strongly adsorbed to the surface of a nanoscale core. In some embodiments, capping agents provide stabilization and/or prevent aggregation of nanoscale cores.

Exemplary capping agents include organic agents such as citrate, citric acid, ascorbic acid, ascorbate, palmitoylascorbate, tetrakis(hydroxymethyl)phosphonium chloride, amino acids, and any combination thereof.

Typically, capping agents are different from surface primers (e.g., a substance (e.g., MPTMS, APTMS), or polymer (e.g., polyethyleneglycol-(PEG)-thiol)) in that surface primers are added after nanoscale core synthesis. In some such instances, some or all of the capping agents are ultimately removed from a nanoscale core by the surface primers.

In contrast to traditional surface priming methods wherein capping agents are displaced by surface primers, in the present disclosure the capping agent itself is employed to enable core encapsulation.

By using the already-present capping agents to enable encapsulation instead of adding additional surface primers, a higher proximity and density of SE(R)RS-active agents on the nanoscale core is achieved.

In some embodiments, a capping agent is displaced by a dopant entity. In many embodiments, a capping entity does not form a covalent bond with a nanoscale core's surface.

Agents

Particles described herein can be prepared with dopant entities that are agents intended for administration or delivery. In some embodiments, such an agent remains associated with the particle after administration of the particle; in some embodiments, such an agent is released or otherwise disassociated from the particle after administration Any of a wide range of agents may be used in accordance with the present invention. Exemplary agents may include, but are not limited to, therapeutic agents and/or imaging agents. For example, agents may be or may comprise any therapeutic agents (e.g., antibiotics, NSAIDs, angiogenesis inhibitors, neuroprotective agents, etc.), cytotoxic agents, diagnostic agents (e.g., contrast agents; radionuclides; and fluorescent, luminescent, magnetic moieties, etc.), targeting agents, prophylactic agents (e.g., vaccines), and/or nutraceutical agents (e.g., vitamins, minerals, etc.), or other substances that may be suitable for introduction to biological tissues, including pharmaceutical excipients and substances for cosmetics, and the like. In some embodiments, agents are selected from the group consisting of MRI agents, PET tracers, SPECT tracers, fluorochromes, CT agents US agents, and any combination thereof.

In some embodiments, an agent can be associated with a particle. In certain embodiments, agents are attached directly or indirectly to an encapsulant. In certain embodiments, agents are incorporated within an encapsulant.

MRI Agents

An agent can be an MRI agent. In some embodiments, the amount or number of MRI agents associated with an encapsulant can be about 1 to 10,000,000 MRI agents or about 5000 to 500,000 MRI agents. In general, larger surface areas of encapsulant contain larger numbers of MRI agents. In some embodiments, all or a portion of MRI agents can be directly attached on the encapsulant surface. For example, an MRI agent can be Gd(-salts), and Gd may be directly attached to the surface of an encapsulant and not attached via a linker compound such as DOTA which in turn is conjugated to the surface. In some embodiments, all or a portion of MRI agents are indirectly attached on the encapsulant surface via one or more linkers. In certain embodiments, in addition to all of MRI agents being directly attached on an encapsulant or all being indirectly attached on the encapsulant, the ratio of the directly against indirectly attached MRI agent is about 1:10 to about 10:1 or about 1:1. In certain embodiments, the number of MRI agents directly attached and indirectly attached can be varied to achieve a certain signal. The amount of MRI agents associated with an encapsulant can be controlled by pH, temperature, ionic strength, and/or identity of MRI agent/encapsulant. Thus, the amount attached directly and indirectly can be controlled and selected to achieve desired results. U.S. Patent Application Publication No. 20120179029, the contents of which is incorporated herein by reference in its entirety, discusses, among others, probes, methods of using probes, methods of making the probe, methods of imaging a condition (e.g., pre-cancerous tissue, cancer, or a tumor), methods of planning resection of a brain tumor, methods of imaging a brain tumor, and the like.

Some embodiments of a MRI agent can be or include Gd(-salts), iron oxide, paramagnetic chemical exchange saturation transfer (CEST) agents, $^{19}$F active materials, manganese, melanin, or a substance that shortens or elongates T1 or T2 and a combination thereof. In certain embodiments, a Gd MRI agent can be a compound such as DOTA-Gd, DTPA-Gd, Gd within a polymeric chelator, and Gd immobilized by negative charges on an encapsulant. In certain embodiments, an iron oxide MRI agent can be a compound such as a small paramagnetic iron oxide (SPIO) or an ultrasmall SPIO with or without a dextran or other stabilizing layer. In certain embodiments, a paramagnetic CEST MRI agent can be a compound such as lanthanide complexes.

In some embodiments, MRI agents can be linked to an encapsulant surface via a linkage such as a maleimide linkage, NHS ester, click chemistry, or another covalent or non-covalent approach or a combination thereof. In some embodiments, MRI agents can also be loaded without addition of any exogenous agent, for example, only encapsulant and MRI agent.

Alternatively or in addition to MRI agents, one or more other agents can be associated with a particle. Exemplary diagnostic agents including a PET (e.g., $^{18}$F, $^{64}$Cu, $^{11}$C, $^{13}$N $^{15}$O, and the like), SPECT (e.g., $^{99}$Tc, $^{67}$Ga, $^{192}$Ir and the like), fluorochrome (e.g., Alexa 647, Alexa 488 and the like), radio nuclide (e.g., alpha-emitting radionuclides (e.g., At-211, Bi-212, Bi-213, Ra-223, and Ac-225), beta-emitting radionuclides (e.g., Cu-67, Y-90, Ag-111, I-131, Pm-149, Sm-153, Ho-166, Lu-177, Re-186, and Re-188)), and the like, can be associated with a particle and be detected using appropriate detection systems. In certain embodiments, the use of a radionuclide can be used to induce signal via Cerenkov radiation.

Targeting Agents

An agent can be a targeting agent (e.g., a chemical or biological agent) having an affinity for a target in the living host, where the agent is associated with a particle (e.g., an encapsulant of the particle). In some embodiments, a particle can be used to image, detect, study, monitor, evaluate, and/or screen a disease, condition, or related biological event corresponding to the target.

In some embodiments, a targeting agent can function to cause a particle to interact with a molecule(s). In some embodiments, a targeting agent can have an affinity for a cell, a tissue, a protein, DNA, RNA, an antibody, an antigen, and the like, that may be associated with a condition, disease, or related biological event, of interest. In some embodiments, a targeting agent can function to target specific DNA, RNA, and/or proteins of interest. In some embodiments, a targeting agent can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, that have an affinity for a condition, disease, or related biological event or other chemical, biochemical, and/or biological events of the condition, disease, or biological event. In some embodiments, a targeting agent can include: sequence-specific DNA oligonucleotides, locked nucleic acids (LNA), and peptide nucleic acids (PNA), antibodies, and small molecule protein receptors.

Other Agents

In accordance with the present disclosure, a particle can include one or more agents for delivery after administration/implantation. Such an agent may be or comprise small molecules, large (i.e., macro-) molecules, or any combinations thereof. Additionally or alternatively, an agent can be a formulation including various forms, such as liquids, liquid solutions, gels, hydrogels, solid particles (e.g., microparticles, nanoparticles), or combinations thereof.

In representative, non-limiting, embodiments, an agent can be selected from among amino acids, vaccines, antiviral agents, nucleic acids (e.g., siRNA, RNAi, and microRNA agents), gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, vitamins and/or any combination thereof. In some embodiments, an agent may be selected from suitable proteins, peptides and fragments thereof, which can be naturally occurring, synthesized or recombinantly produced.

In some embodiments, an agent is or comprises a biologic. Examples of biologics including, but are not limited to, monoclonal antibodies, single chain antibodies, aptamers, enzymes, growth factors, hormones, fusion proteins, cytokines, therapeutic enzymes, recombinant vaccines, blood factors, and anticoagulants. Exemplary biologics suitable for use in accordance with the present disclosure are discussed in S. Aggarwal, *Nature Biotechnology*, 28:11, 2010, the contents of which are incorporated by reference herein.

In some embodiments, compositions and methods in accordance with the present application are particularly useful to deliver one or more therapeutic agents.

In some embodiments, a therapeutic agent is a small molecule and/or organic compound with pharmaceutical activity. In some embodiments, a therapeutic agent is a clinically-used drug. In some embodiments, a therapeutic agent is or comprises an anti-cancer agent, antibiotic, antiviral agent, anesthetic, anticoagulant, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

Exemplary anticancer agents include, but are not limited to, a cytokine, a chemokine, a growth factor, a photosensitizing agent, a toxin, an anti-cancer antibiotic, a chemotherapeutic compound, a radionuclide, an angiogenesis inhibitor, a signaling modulator, an anti-metabolite, an anti-cancer vaccine, an anti-cancer oligopeptide, a mitosis inhibitor protein, an antimitotic oligopeptide, an anti-cancer antibody, an anti-cancer agent, antibiotic, an immunotherapeutic agent, hyperthermia or hyperthermia therapy, a bacterium, radiation therapy and a combination of such agents. In some examples, an anticancer agent is cisplatin, carboplatin, gemcitabine, irinotecan, an anti-EGFR antibody, an anti-VEGF antibody and any combinations thereof.

A therapeutic agent used in accordance with the present application can be or can comprise an agent useful in combating inflammation and/or infection. A therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof. Other anti-microbial agents such as copper may also be used in accordance with the present invention. For example, anti-viral agents, anti-protazoal agents, anti-parasitic agents, etc. may be of use. Additionally or alternatively, a therapeutic agent may be an anti-inflammatory agent.

A therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may include a therapeutic gene as known in the art. In some embodiments, a therapeutic agent is a non-viral vector. Typical non-viral gene delivery vectors comprise DNA (e.g., plasmid DNA produced in bacteria) or RNA. In certain embodiments, a non-viral vectors is used in accordance with the present invention with the aid of a delivery vehicle. Delivery vehicles may be based around lipids (e.g., liposomes) which fuse with cell membranes releasing a nucleic acid into the cytoplasm of the cell. Alternatively or alternatively, peptides or polymers may be used to form complexes (e.g., in form of particles) with a nucleic acid which may condense as well as protect the therapeutic activity as it attempts to reach a target destination.

Uses and Applications

Provided are particles and methods that can be used in various applications. Embodiments of the present disclosure can be used to image, detect, study, monitor, and/or evaluate, any malignant or atypical cells or tissues, including a condition or disease such as pre-cancerous tissue, cancer, or a tumor. In some embodiments, compositions and methods described herein are particularly useful for solid tumors. Exemplary solid tumors include, but are not limited to, malignant tumors of brain, lung, breast, ovary, stomach, pancreas, larynx, esophagus, testes, liver, parotid, biliary tract, colon, rectum, cervix, uterus, endometrium, kidney, bladder, prostate, thyroid, head and neck, melanomas, gliomas, neuroblastomas, neuroendocrine tumors, and the like.

Figure 27:
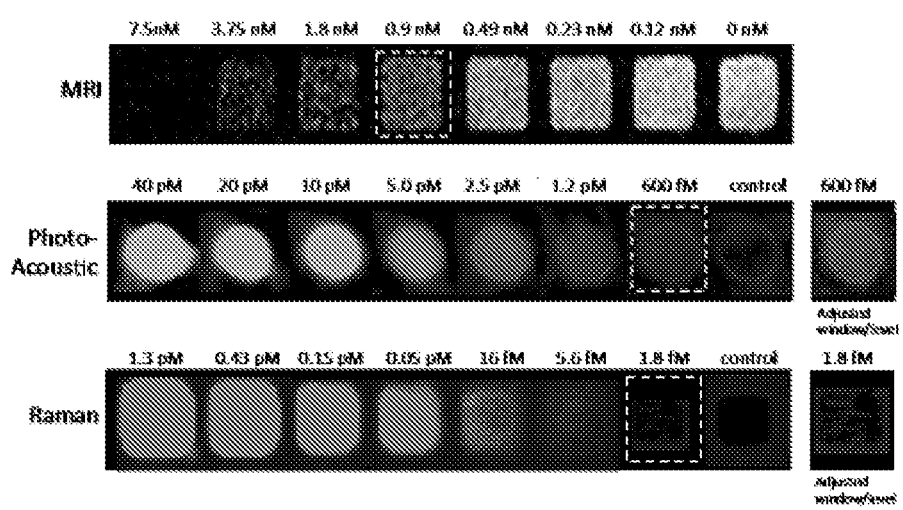
FIG. 27 presents a detection threshold chart of MPR-Nanostars for three imaging modalities—MRI, photo-acoustic, and Raman. The indicated concentrations of MPR-Nanostars were embedded in 1% agarose in well-plates and imaged. The well with the lowest concentration of MPR-Nanostars that could still be detected is indicated with a white dashed box (adjusted window/level setting for improved visibility of photoacoustic and Raman data on the right) and represents the detection threshold for that respective imaging modality (0.9 nM for MRI, 600 fM for Photoacoustic, 1.6 fM for Raman imaging).
Figure 28:
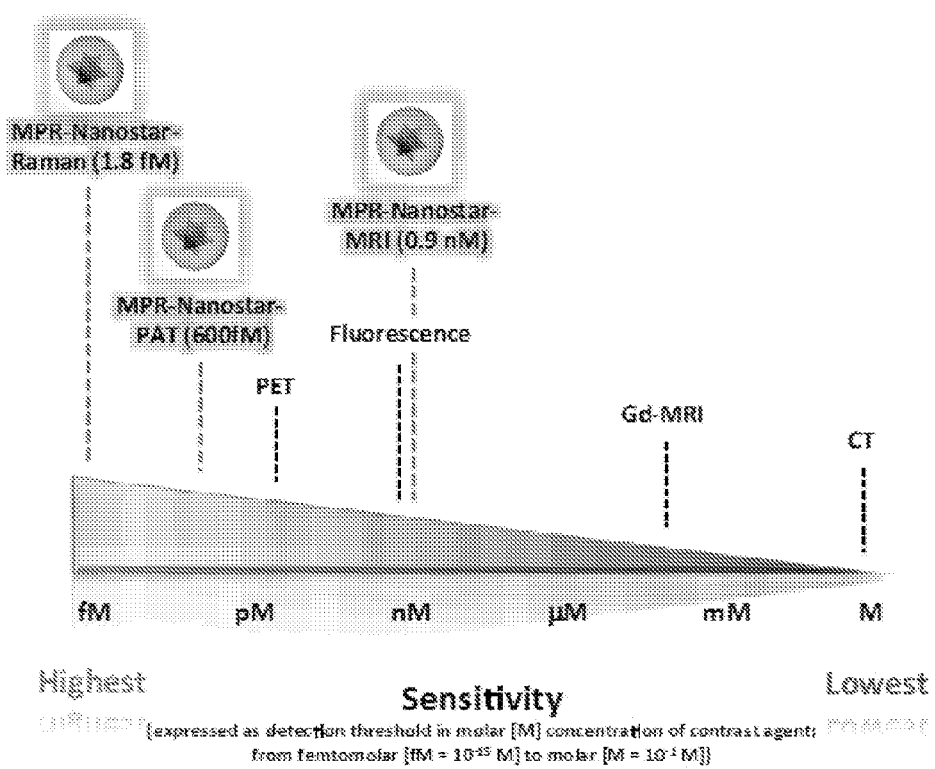
FIG. 28 presents a chart comparing the detection sensitivity between MPR-Nanostars and established imaging modalities, where the values for MPR-Nanostars were derived from data in FIG. 21; values for positron-emission-tomography (PET), fluorescence, MRI and CT were derived from Debbage P, Jaschke W. Molecular imaging with nanoparticles: giant roles for dwarf actors. Histochemistry and cell biology. 2008; 130(5):845-75. Epub 2008/10/01. doi: 10.1007/s00418-008-0511-y. PubMed PMID: 18825403; Lusic H, Grinstaff M W. X-ray-Computed Tomography Contrast Agents. Chemical reviews. 2012. Epub 2012/12/06. doi: 10.1021/cr200358s. PubMed PMID: 23210836; and Massoud T F, Gambhir S S. Molecular imaging in living subjects: seeing fundamental biological processes in a new light. Genes & development. 2003; 17(5):545-80. Epub 2003/03/12. doi: 10.1101/gad.1047403. PubMed PMID: 12629038. Note that MPR-Raman and MPR-PAT are approximately 6 and 4 orders of magnitude, respectively, more sensitive than fluorescence imaging. MPR-MRI (due to the clustering of ferumoxytol in the MPR core) is approximately 4 orders of magnitude more sensitive than conventional MRI using clinically approved small molecule Gd-contrast agents (MPR-Nanostar-MRI approaches the sensitivity of fluorescence).

It is important to note that because of the unparalleled Raman signal intensity (which enables low detection threshold) and the unique pharmacokinetic behavior (e.g., "enhanced permeability and retention" (EPR) effect) of a SE(R)RS particle described here, in some embodiments, any kind of cancer (not only one particular kind of cancer), can be imaged, detected and treated. In some embodiments, a SE(R)RS particle has a detection threshold as low as, or below about 100 fM, about 50 fM, about 20 fM, about 10 fM, about 5 fM or even about 1 fM. Example detection threshold results are shown in FIG. 27.

In some embodiments, provided particles can be associated with a cell (e.g., located within a cell or attached to cell surface) for cell tracking.

Exemplary administrations of particles include but are not limited to oral, intravenous, sublingual (i.e., under a tongue), respiratory, or intraoperative administrations. It is recognized in the present application that provided particles and methods can be of particular interest in and surprisingly useful for detecting residual tumor in surgery.

In some embodiments, particles can be used to image, detect, study, monitor, evaluate, and/or screen a sample or subject (e.g., whole-body or a portion thereof). Embodiments of the present disclosure include a method of planning resection of a tumor, evaluating a tumor, intraoperative tumor resection guidance, verification of clean margins in vivo or ex vivo, or the like. In some embodiments, provided method can include a pre-operative and intra-operative procedure time frame and can also include the post-operative procedure time frame to study removed tissue. In some embodiments, a method can include administering an appropriate amount of a particle (e.g., an effective dose(s)) so that the particle is detectable in a tumor for a few days to a week or ten days (or other suitable time period). If needed, larger doses can be administered to maintain a detectable amount of the particle in the tumor for a desired predetermined time period. In addition, multiple doses of a particle can be administered during the time frame of the procedure.

Now referring to methods of evaluating a tumor, after a particle has been administered to the subject, the following can be obtained during one or more of the pre-operative, intra-operative, and/or post-operative time frames of the procedure: a MRI signal, a photoacoustic signal, and a Raman signal. Each of the signals can be included in an information set (e.g., signal, location of the signal, time of the signal, intensity of the signal, and the like, wherein one or more of these or a combination can be referred to as "data" as discussed below) that can be analyzed. An appropriate energy can be used to produce the photoacoustic and Raman signals, as described in more detail in U.S. Patent Application Publication No. 20120179029.

In some embodiments, an MRI signal can be used to produce an image corresponding to one or more of: the localization of the whole tumor, macroscopic delineation of the whole tumor, and residual portions of the tumor. The first two can be measured or detected during the pre-operative time frame of the procedure, while the last is measured or detected during the post-operative time frame of the procedure. A MRI signal can be measured or detected using an MRI system such as 15 T, 11 T, 9.4 T, 7 T, 3 T, 1.5 T, or 0.5 T or less, which is well known in the art.

In some embodiments, a photoacoustic signal is used to produce an image corresponding to the tumor with deep tissue penetration (e.g., about 4 to 10 cm). A photoacoustic signal can be measured using a photoacoustic system described in U.S. Patent Application Publication No. 20120179029.

In some embodiments, a Raman vibrational signal can be used as a guide to defining the tumor margins as well as to produce an image of a portion of the brain (e.g., edges of transition from tumor to brain tissue). A Raman vibrational signal can be measured using a Raman system as described herein (e.g., raster scanning or point by point scanning).

In some embodiments, an MRI signal, a photoacoustic signal, and a Raman signal (or the corresponding information set), can be used to image and/or determine the location, relative position, and/or the presence of a particle at a particular location, of one or more of: the tumor and the tumor margins, during the operative procedure. The signals (or the corresponding information set) can be used alone or in combination at any given point during the procedure. Signals (or the corresponding information set) can all be used to facilitate a superior resection procedure since at certain points of the procedure a single type of particle can be used to obtain each type of signal. This is advantageous because repeated injection of contrast agents can show decreased efficacy and may induce toxicity.

Now referring to methods of planning resection of a tumor as an example, after a particle has been administered to a subject, the following can be obtained during one or more of the pre-operative, intra-operative, and/or post-operative time frames of the procedure: MRI data, photoacoustic data, and Raman data. Data can be obtained by appropriate processing of each type of signal received to produce an image or monitored although not processed into an image. In some embodiments, one or more types data can be used to visualize (e.g., image) the tumor. Two or more of the types of data can be combined to visualize (e.g., produce an image) of the tumor. Processing of the signals to produce data is known in the art (e.g., MRI data processing).

In some embodiments, an MRI data corresponds to one or more of: tumor localization and macroscopic delineation of the tumor. In some embodiments, an MRI data can be used to obtain the whole tumor in the pre-operative time frame as well as obtain intra-operative or post-operative data regarding any remaining tumor.

In some embodiments, a photoacoustic data corresponds to a tumor with deep tissue penetration (e.g., about 5 to 10 cm deep into the subject). In some embodiments, a photoacoustic data corresponds to the intra-operative time frame of the procedure.

In some embodiments, a Raman data corresponds to the tumor margins. In some embodiments, a Raman data corresponds to the intra-operative time frame of the procedure and can also be used in the post-operative time frame of the procedure.

In some embodiments, MRI data, photoacoustic data, and Raman data can be used to determine the location of one or more of: the tumor and the tumor margins, during an operative procedure. A data can be used alone or in combination at any given point during the procedure. The data can all be used to facilitate a superior resection procedure since at certain points of the procedure a single type of particle can be used to obtain each type of data. This is advantageous because each of the three modalities has complementary strengths such as greater depth penetration, greater spatial resolution, greater sensitivity, and greater specificity.

Although the methods described above are directed to tumors, other tissue types can be substituted for the tumor. For example, pre-cancerous or cancerous cells or even noncancerous cells such as inflammation or infection can be treated in the similar way.

EXEMPLIFICATION

The following examples demonstrate the development of a novel multimodal concept that allows straightforward detection of residual tumor in the operating room. There are three components: A) an injectable particle, B) an existing clinical MR scanner, and C) a hand-held Raman detector.

Simply put, the method uses a single intravenous injection of a nanoscale core/encapsulant particle, which can visualize both the tumor outline in 3D to provide a roadmap (with MRI, PET, SPECT, CT, US etc. preoperatively and/or intraoperatively) and determine residual tumor with microscopic resolution in real-time with a Raman and/or photoacoustic hand-held scanner.

The examples and many embodiments disclosed herein employ oscillating electric fields, which induce oscillations in the electron clouds of molecules, referred to as induced dipoles. These oscillating electron clouds in turn generate light. The light generated by the oscillating dipole is referred to as scattered light, and the intensity of the scattered light is dependent upon the amplitude of the dipole oscillation (the amplitude of the electron cloud oscillation).

The amplitude of a molecule's induced dipole is proportional to the amplitude of the electric field incident upon it (Eq. 1).

$$P = \alpha E \qquad \text{Eq. 1}$$

where P is the induced dipole, and E is the incident electric field. The proportionality constant $\alpha$ is called the molecule's polarizability, and it is dependent upon the nuclear coordinates for certain vibrational modes (the polarizability is a function of the position of the nuclei and will vary for certain vibrational modes as the nuclei oscillate).

The time-dependent equation of a simple oscillating electric field is $$E = E_0 \cos(2\pi v_0 t) \qquad \text{Eq. 2}$$

where $E_0$ is the [maximum] amplitude of the electric field, $v_0$ is the frequency of the oscillating electric field and t is the time. For a given vibrational mode, the instantaneous nuclear coordinate (position of the nuclei) is $$dQ = Q_0 \cos(2\pi v_{vib} t) \qquad \text{Eq. 3}$$

where $Q_0$ is the maximum displacement of the nuclei relative to their equilibrium position for a given vibrational mode, $v_{vib}$ is the vibrational frequency, and t is time. Since the polarizability is a function of the nuclear coordinates, it can be expressed as a taylor series about the equilibrium value of $\alpha$ in terms of the variable Q (the nuclear coordinate). As a simplification, which holds well for relatively small nuclear displacements, the Taylor series can be approximated by the first two terms:

$$\alpha = \alpha_0 + \left(\frac{d\alpha}{dQ}\right) dQ \qquad \text{Eq. 4}$$

Inserting equations 2 and 4 into equation 1 yields:

$$P = \left(\alpha_0 + \left(\frac{d\alpha}{dQ}\right) dQ\right)[E_0 \cos(2\pi v_0 t)] \qquad \text{Eq. 5}$$

Inserting equation 4 into equation 5 and simplifying gives:

$$P = \alpha_0 E_0 \cos(2\pi v_0 t) + \left(\frac{d\alpha}{dQ}\right)[Q_0 \cos(2\pi v_{vib} t)][E_0 \cos(2\pi v_0 t)] \qquad \text{Eq. 6}$$

Finally, applying the trigonometric identity $\cos(a)\cos(b) = \frac{1}{2}[\cos(a+b) + \cos(a-b)]$ yields:

$$P = \alpha_0 E_0 \cos(2\pi v_0 t) + \left(\frac{d\alpha}{dQ}\right)\left(\frac{Q_0 E_0}{2}\right)\{\cos[2\pi(v_0 - v_{vib})t] + \cos[2\pi(v_0 + v_{vib})t]\}. \qquad \text{Eq. 7}$$

Equation 7 demonstrates that an oscillating electric field will induce a dipole in a molecule which can oscillate at three frequencies: $v_0$, $v_0-v_{vib}$, and $v_0+v_{vib}$. The first of these frequencies is equal to the frequency of the incident electric field, and the corresponding equal-frequency scattering is referred to as elastic, or Rayleigh, scattered light. The second frequency is lower than the incident electric field's frequency, and corresponding lower-frequency inelastic scattering is referred to as Raman Stokes scattering. The last of the three frequencies is higher than the incident electric field frequency, and the corresponding higher-frequency inelastic scattering is referred to as Raman Anti-Stokes scattering.

In order to increase the intensity of the Raman scattered light, the overall scattering intensity can be increased, or the ratio of Raman scattering to total scattering can be increased. The overall scattering intensity is increased when the number and/or amplitude of induced dipoles is increased. From Equation 1 it can be seen that increasing either the polarizability or the incident electric field will increase the amplitude of the induced dipole. Both of these factors are enhanced for molecules close to the surface of a noble-metal particle. Specifically, molecules bound to the particle exist as a particle-molecule hybrid which is characterized by a dramatically increased polarizability relative to the unbound molecule, as the particle's (conduction band) electrons are much more susceptible to incident electric fields than are the molecule's. Furthermore, the dimensions of the particle can be tuned such that they are much smaller (e.g., <10%) than the wavelength of incident light, so that the coordinated oscillation of conduction electrons—called the localized surface plasmon resonance—effectively concentrates the electric field of incident electromagnetic radiation at its surface, providing a greatly-enhanced electric field for molecules situated nearby (e.g., within approximately 20 nm of the particle surface). Further enhancement of the electric field can be achieved by tuning the morphology of the particle to incorporate "hot-spots," such as the tip of a prolate-spheroid wherein large amounts of charge are corralled into very small regions.

The ratio of Raman-to-overall scattered light can be increased by shifting the incident electric field frequency to an electronic excitation frequency of the molecule, or by choosing a molecule which has an electronic excitation frequency at the fixed electric field frequency. The reason that this increases the ratio of Raman-to-overall scattering is that the lifetime of the "virtual" excited state that precedes emission of scattered light is significantly increased at excitation frequencies. Because of this longer excitation, the initial and final nuclear coordinates become further displaced than they would have for a non-resonant molecule (the nuclei have more time to move before the virtual state de-excites). This large change in nuclear coordinates results in a shift in the favored vibrational state to which the virtual excited state relaxes, as described by the Franck-Condon principle. Thus, resonant dyes yield much more intense Raman scattering. An important note is that a similar resonance effect can be achieved by means of a charge transfer between the molecule and the particle.

By combining resonant agents with particles that have been optimized for electric field enhancement, both the total scattering and ratio of Raman-to-total scattering become drastically increased, and the Raman scattering intensity per molecule is maximized. The final step toward generating the theoretically maximum-intensity SE(R)RS particles is to optimize the number of dye molecules at the surface of the particle. This optimum concentration of resonant dye molecules is generally much higher than that which could be achieved with current primer-based protocols for generating SE(R)RS particles. In the latter case, for silica in particular, the encapsulant is grown onto the particle upon binding to molecules, which prime the surface, typically amino- or mercaptosilanes. In these cases, the stabilizing or surface priming agents bind more tightly to the particle surface than capping agents, such as citrate or ascorbic acid, which do not contain nitrogen, sulfur, or other strongly-binding atoms. This means that the competitive equilibrium, which exists for surface binding, namely the equilibrium describing the displacement of capping molecules and the binding of Raman-active molecules to the particle surface, is strongly disfavored upon the addition of surface priming or stabilizing agents relative to their absence. In addition, previously unoccupied binding sites will be blocked by the surface primers and therefore not accessible for binding of the resonant agents. Therefore, it is the present disclosure that first recognizes that the number of Raman-active molecules present on the particle surface can be optimized by encapsulation or stabilization without use of additional surface primers or polymers.

Example 1: Synthesis of SE(R)RS Particles

Gold nanostar-shaped cores were synthesized by rapidly adding 20 mM $HAuCl_4$ to 40 mM ascorbic acid at 4° C. The as-synthesized ascorbate-stabilized gold nanostars (~75 nm, 1 nM) were collected by centrifugation (3,500×g, 15 min) and dialyzed overnight. The dialyzed gold nanostars were coated with dye-embedded silica via a typical Stöber method. In brief, the dialyzed gold nanostars were added to ethanol to which the resonant Raman dye, TEOS and ammonia were added and allowed to react for 1 hour. The particles were isolated by centrifugation (3,500×g, 15 min) and washed with ethanol. To enable PEGylation, the silica surface was modified with sulfhydryl-groups by heating the silica-coated nanostars for 1 hour at 72° C. in ethanol containing 1% (v/v) MPTMS. The nanostars were washed with ethanol to rid of the MPTMS and redispersed in 10 mM MES buffer (pH 7.1) containing 1% (w/v) methoxy terminated (m)$PEG_{2000}$-maleimide. The maleimide-$mPEG_{2000}$ was allowed to react with the sulfhydryl-modified silica surface for 2 hours at ambient conditions. The PEGylated resonant Raman active nanostars were washed and redispersed in filter-sterilized 10 mM MES buffer (pH 7.3) and stored at 4° C. prior to injection. A resultant particle is illustrated in FIG. 1.

A SE(R)RS particle is unique in several ways: 1) It has the highest detection sensitivity of any similar particles reported worldwide. 2) It allows visualizing tumors without the need for a specific targeting moiety on its surface, relying on the "enhanced permeability and retention" (EPR) effect. 3) It has a unique "fingerprint" Raman spectrum allowing detection with unequivocal specificity. 4) It combines a whole-body 3D imaging method with an ultra-high sensitivity detection method for optimal identification of tumor margins. 5) It becomes stably trapped within the tumors, which allows pre-operative staging and intraoperative resection with one single intravenous injection. 6) Rigorous toxicity evaluations of very similar gold-silica-based particles have found them to be safe in vivo.

Example 2: Characterization

Figure 2:
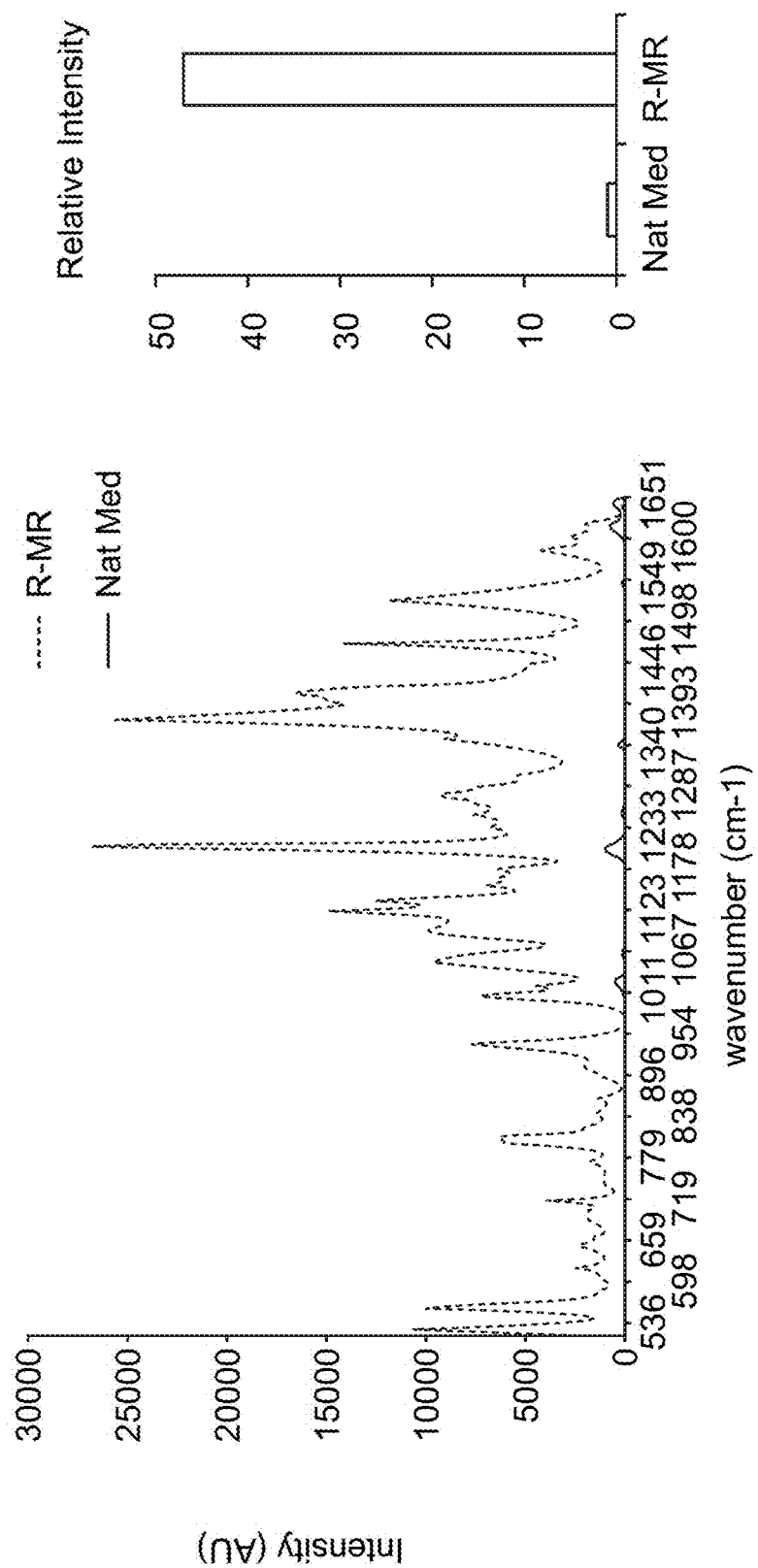
FIG. 2 illustrates direct comparison of the Raman spectral intensity of the SE(R)RS particles to the particles illustrated in Kircher et al., (2012) Nat Med 18 (5):829-834 (Appendix A) currently considered to be the Raman gold standard. As shown in the bar graph, the SE(R)RS particles are 47-times more intense than the particles previously illustrated.

Ultra-High Sensitivity:

As shown in FIG. 2, The SE(R)RS particles synthesized in Example 1 were characterized by transmission electron microscopy (TEM; JEOL 1200EX, USA), size distribution and concentration were determined by nanoparticle tracking analysis (NTA; Nanosight, UK). Raman activities of equimolar amounts of particles were determined on a Renishaw InVIA Raman microscope equipped with a 300 mW 785 nm (near-IR) diode laser and a 1-inch charge-coupled-device detector for a spectral resolution of 1.07 cm$^{-1}$. The Raman spectra were analyzed with WiRE 3.4 software (Renishaw, UK).

Figure 3:
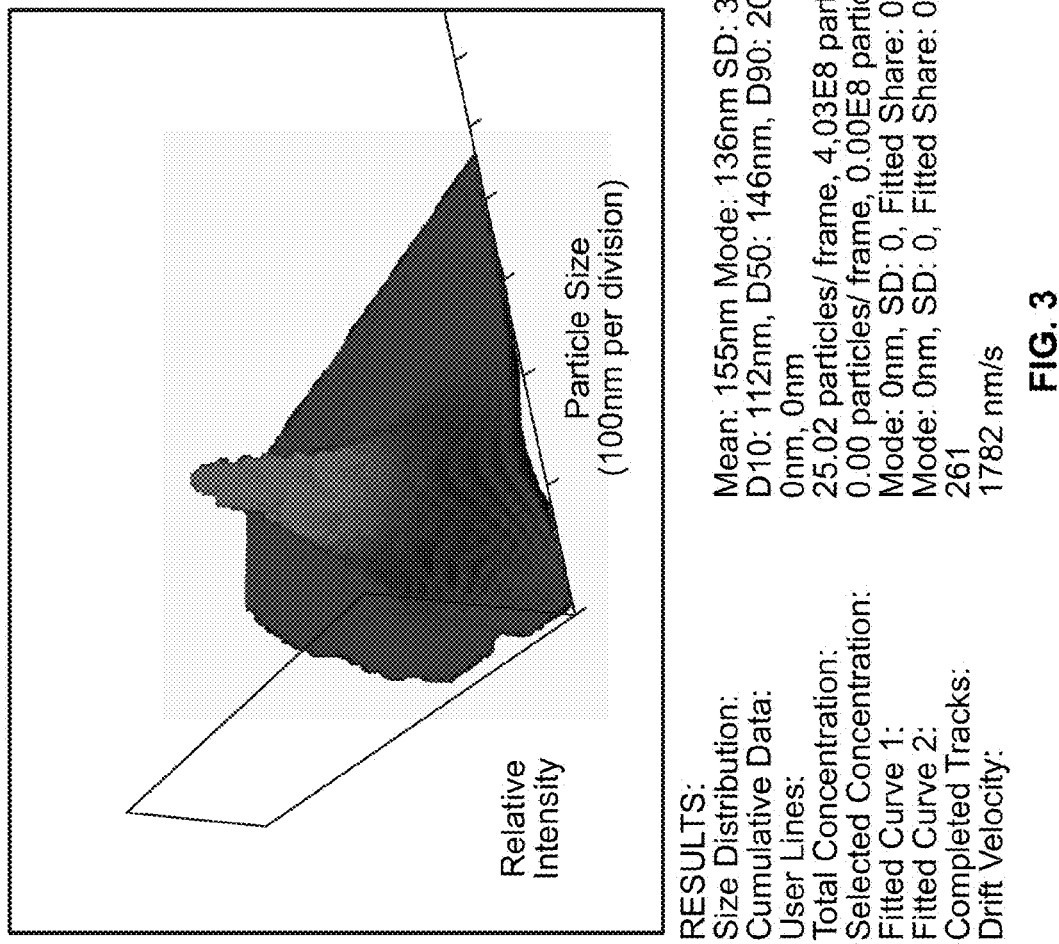
FIG. 3 displays the output of a typical Nanoparticle Tracking Analysis (NTA) scan. NTA enables accurate quantification of particle concentration and size distribution by locking into the light scattered from individual particles and tracing their paths in solution. The concentration is determined by simply counting the number of particles in a defined volume, while size is calculated from the Brownian motion using the Einstein-stokes equation. When combined with the complete morphological information provided by TEM, NTA allows for thorough characterization of the SE(R)RS particles.
Figure 4:
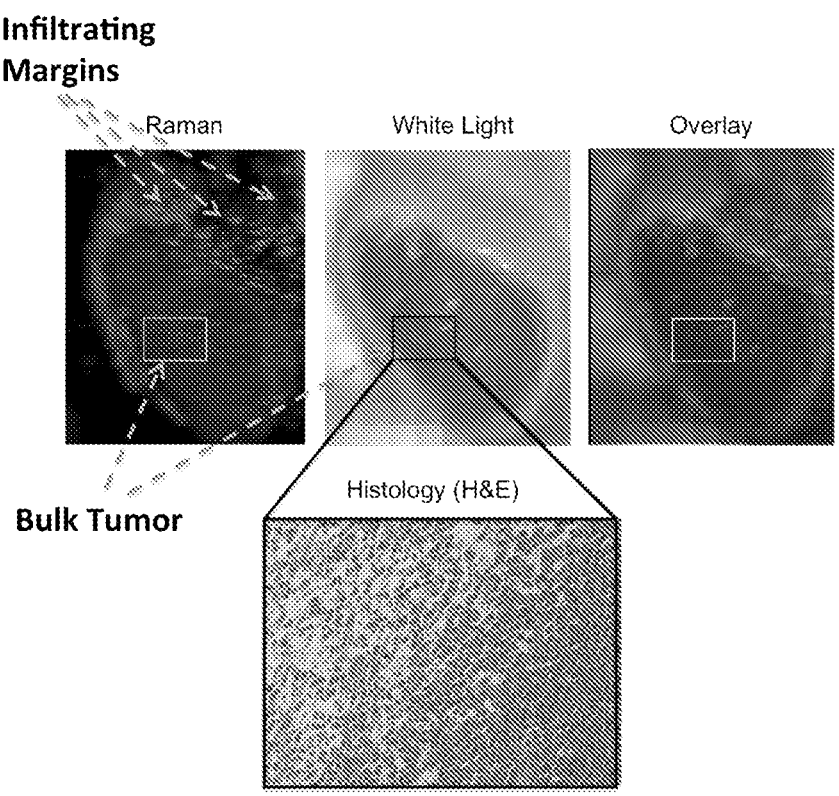
FIG. 4 shows a series of images of a mouse with dedifferentiated liposarcoma implanted in the flank. Note that Raman signal outlines the tumor; there is also Raman signal visible beyond the margins of the tumor seen on the white light (the arrows).
Figure 5:
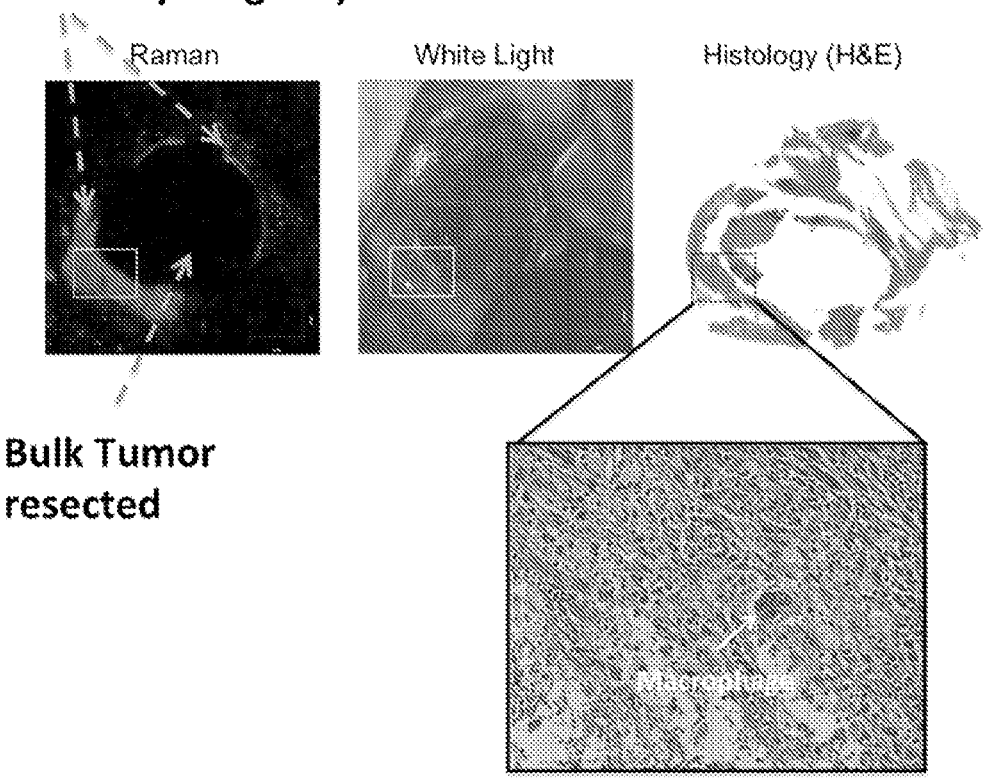
FIG. 5 shows a series of images of the same mouse as shown in FIG. 4, after resection of the bulk tumor by a surgeon using his unaided eye (blinded to Raman signal). Note that there is a residual rim of Raman signal in the resection bed around the resected tumor. Histological evaluation confirmed tumor in the locations of the Raman signal. The arrow indicates tumor-associated macrophage having engulfed SE(R)RS particles.
Figure 6:
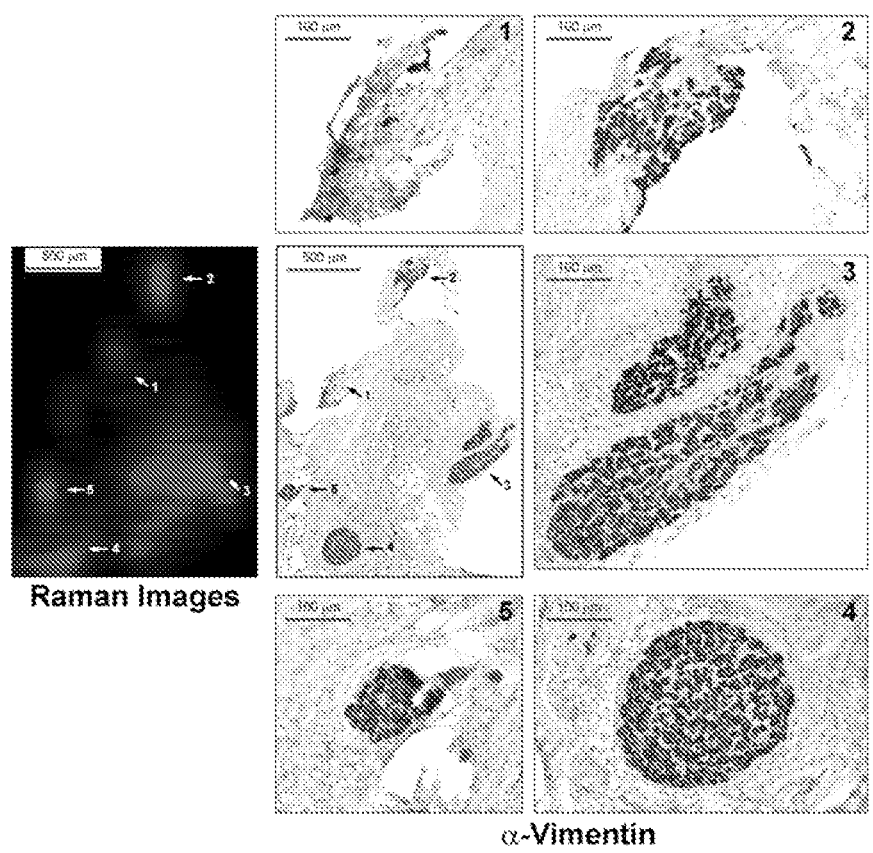
FIG. 6 shows detected microscopic metastases. MPR-Nanostars were injected intravenously (tail vein; 150 µl; 3 nM) into a dedifferentiated human liposarcoma xenograft bearing mouse. Intraoperative Raman image (after 24 h) was taken 1 cm adjacent to the margin of the bulk tumor. It correctly detects multiple micrometastases.
Figure 7:
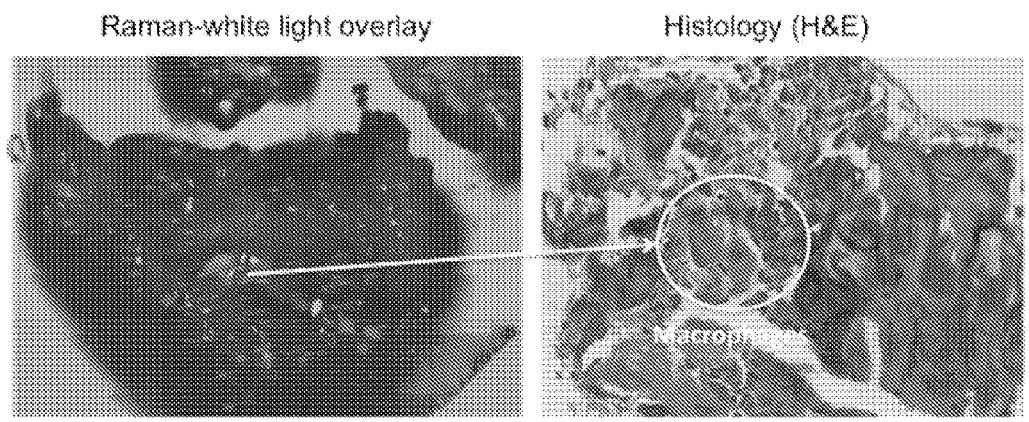
FIG. 7 shows images of the same mouse as shown in FIG. 6 with sarcoma, multiple tiny foci of Raman signal are seen in the resection bed, after the bulk tumor had been resected by a surgeon using white light guidance only (blinded to Raman signal). As histological examination demonstrated, these foci of Raman signal represented tumor-associated macrophages.
Figure 8:
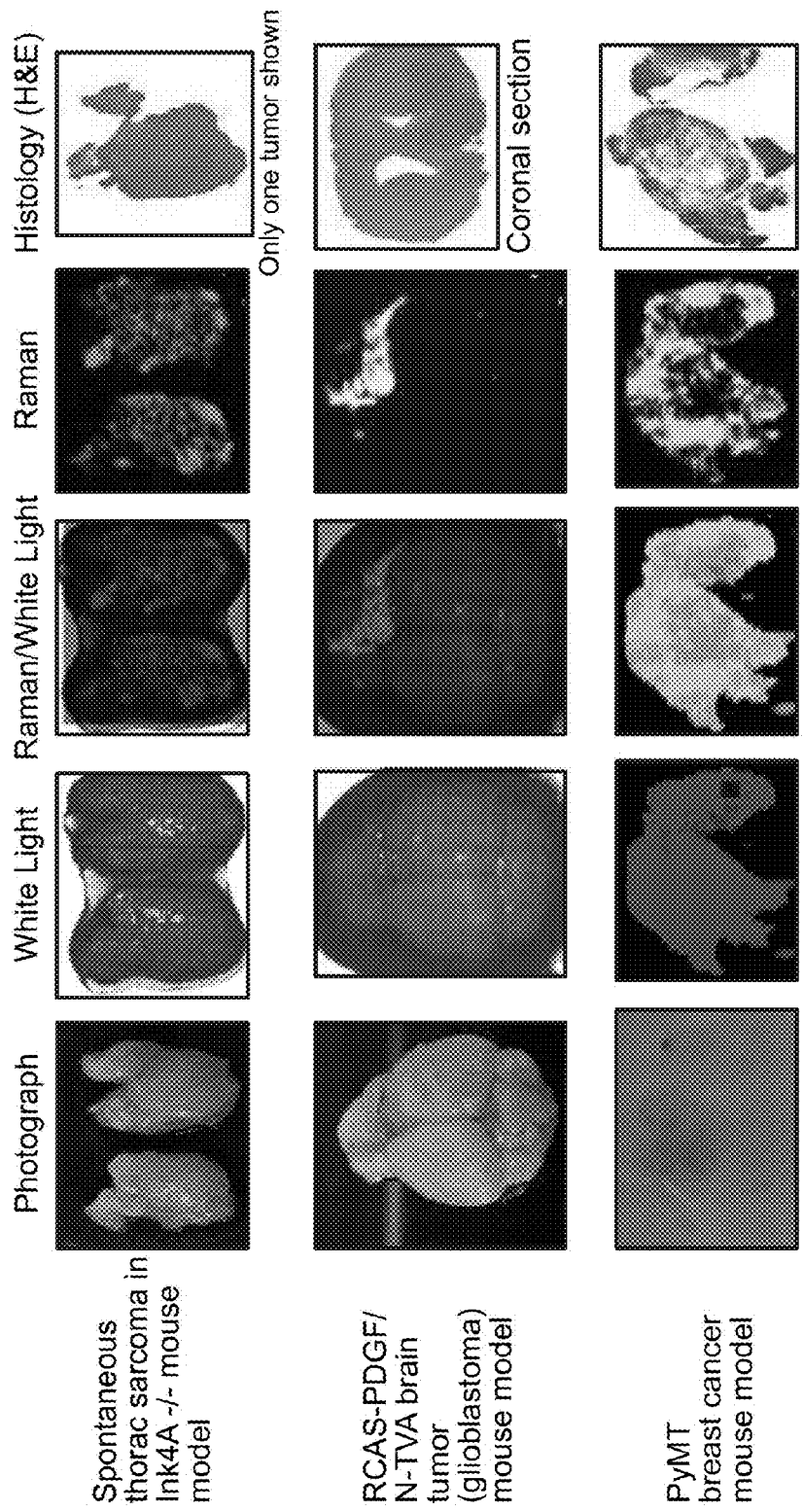
FIG. 8 demonstrates SE(R)RS particles are able to detect a variety of different tumors. Exemplary images are shown two spontaneous sarcomas in an Ink4A−/− mouse model, a brain tumor in the rcas/tv-a model, and a breast cancer in the PyMT model. In each tumor, there was excellent depiction of the tumor by the Raman signal.
Figure 9:
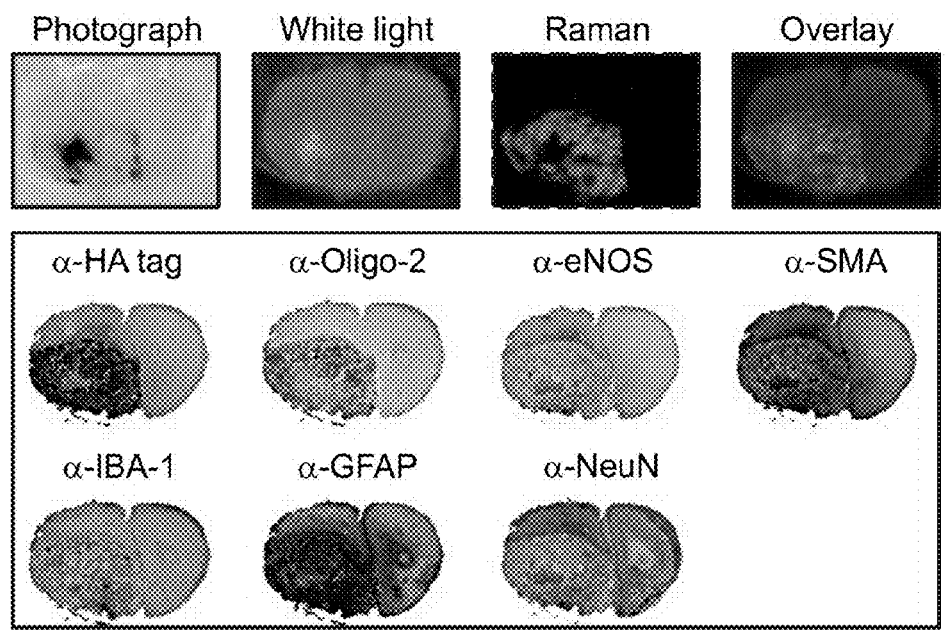
FIG. 9 demonstrates the ability of SE(R)RS particles to outline glioblastomas (rcas/tv-a model). Note the high degree of correlation of Raman signal with the presence of tumor cells (HA-tag, Oligo-2 positive staining). RGD-MPR-Nanostars were injected intravenously via tail vein (150 µl, 3 nM). After 24 hours, mice were sacrificed, perfused via intracardial injection of PBS, brains embedded in paraffin, processed histologically, and imaged with the Renishaw Raman microscope. Adjacent sections were stained for immunohistochemisty. Images are representative of n=5 mice. When the Raman signal is compared to the immunohistochemical staining for glioblastoma cells ($\alpha$(=anti)-HA-tag and Oligo-2), a high degree of congruency is noted. Note the small Raman positive focus outside of the main tumor (eNOS=Endothelial cells; SMA=Smooth Muscle Cells; IBA=Microglia; GFAP=Astrocytes; NeuN=Neurons).
Figure 10:
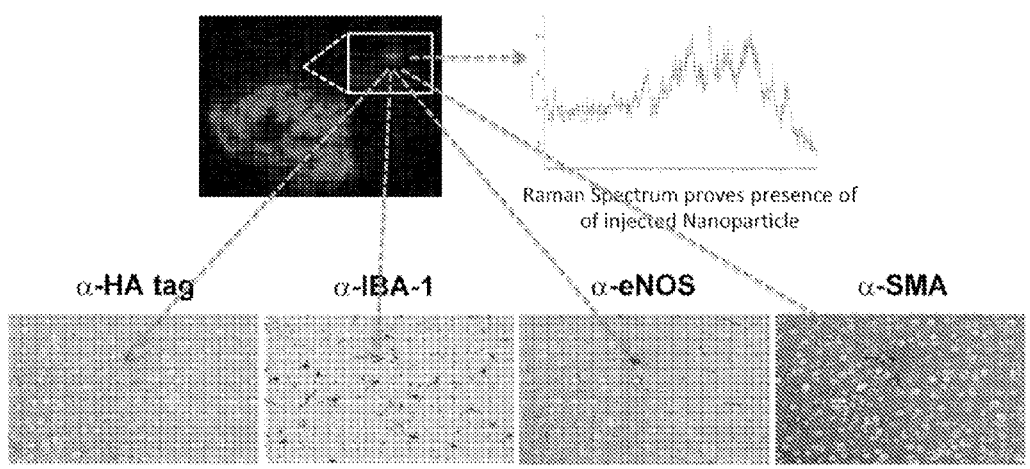
FIG. 10 demonstrates the ability of SE(R)RS particles to depict a single brain tumor cell (micrometastasis away from the main tumor). Insert in Raman image shows magnification of single Raman positive voxel. Raman spectrum proves presence of SE(R)RS particles. Histology proves that this signal correlates to a signal brain tumor cell. Correlation of a single Raman positive pixel (red in upper left image, magnified within the white square) with immunohistochemistry in the RCAS/tv-a glioblastoma model. The same slide as in FIG. 9 was examined at higher magnification. The presented Raman spectrum confirms that the Raman positive pixel truly represents the nanoparticle. HA-tag positive staining confirms that the MPR-Nanostars co-localize with the presence of a glioblastoma cell. Adjacent to the tumor cell are located a microglia cell (IBA-1 positive) and a small blood vessel (eNOS, SMA positive), explaining how the MPR-Nanostars could have been transported to this location. Individual or small clusters of tumor cells located outside of the main tumor are often seen in this mouse model and in human glioblastomas.
Figure 11:
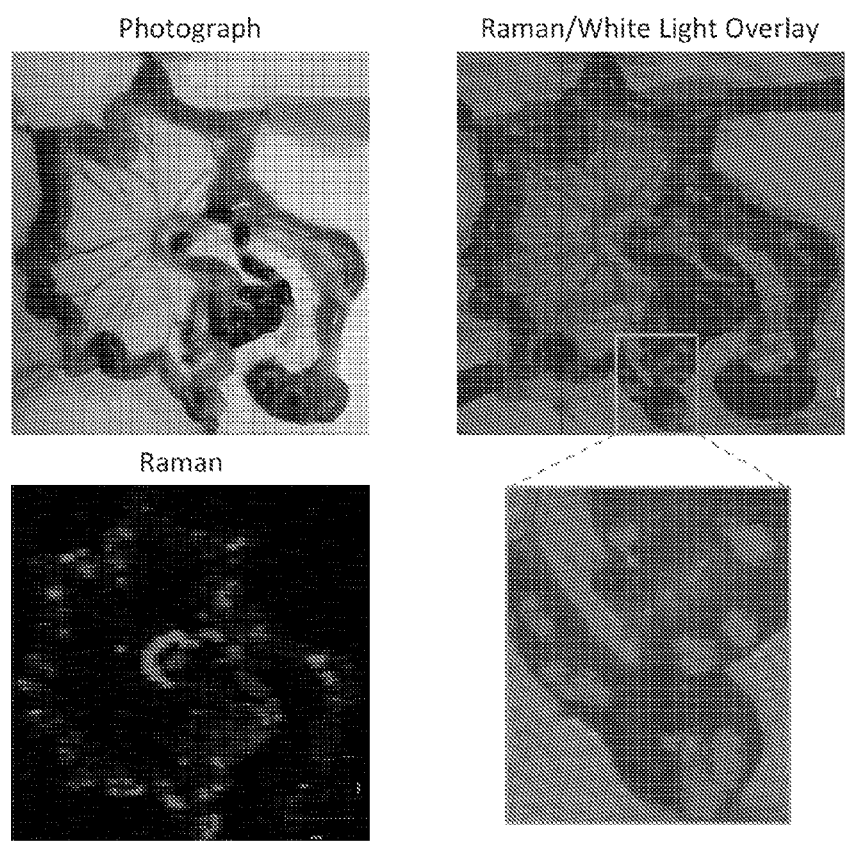
FIG. 11 shows a series of images illustrating using MPR-nanostars to detect submillimeter-sized dysplastic (premalignant) polyps and adenocarcinomas. The illustrated experiment was performed in an $APC^{min}$ mouse, which is a mouse model known to mimic human "adenomatosis polyposis coli" syndrome, a genetic disorder that causes many dysplastic polyps and adenocarcinomas to develop simultaneously. Note that Raman imaging reveals many small foci (less than 1 mm in size) of SERRS-Nanostars uptake within the colon and small bowel of an $APC^{min}$ mouse (excised 24 hours after nanoparticle injection). These foci were then processed with histology (see FIG. 12), which confirmed that they represented dysplastic polyps or adenocarcinomas.
Figure 12:
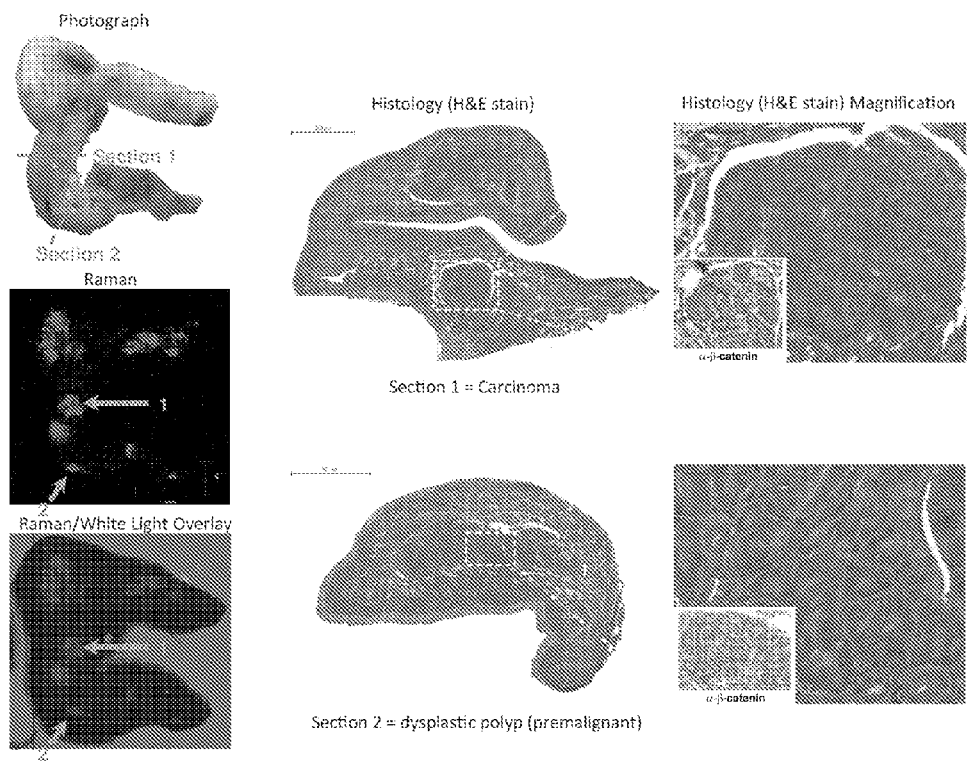
FIG. 12 shows a series of images illustrating using MPR-Nanostars for detecting submillimeter-sized dysplastic (premalignant) polyps and adenocarcinomas—histological confirmation. The presented images show two segments of colon from the mouse in FIG. 11. Two histological cross-sections through the Raman positive areas were obtained and stained with Hematoxylin-Eosin (H&E) and anti-catenin IHC. Section 1 confirm that the lesion to represent an adenocarcinoma, section 2—a dysplastic polyp, and thereby also confirms MPR-Nanostars as described herein are able to detect not only very small colon cancers, but also their premalignant form—dysplastic polyps—which will eventually develop into invasive adenocarcinomas. Among other things, these data confirm that, as described herein, MPR-Nanostars may be used as a new method for early colon cancer detection.
Figure 13:
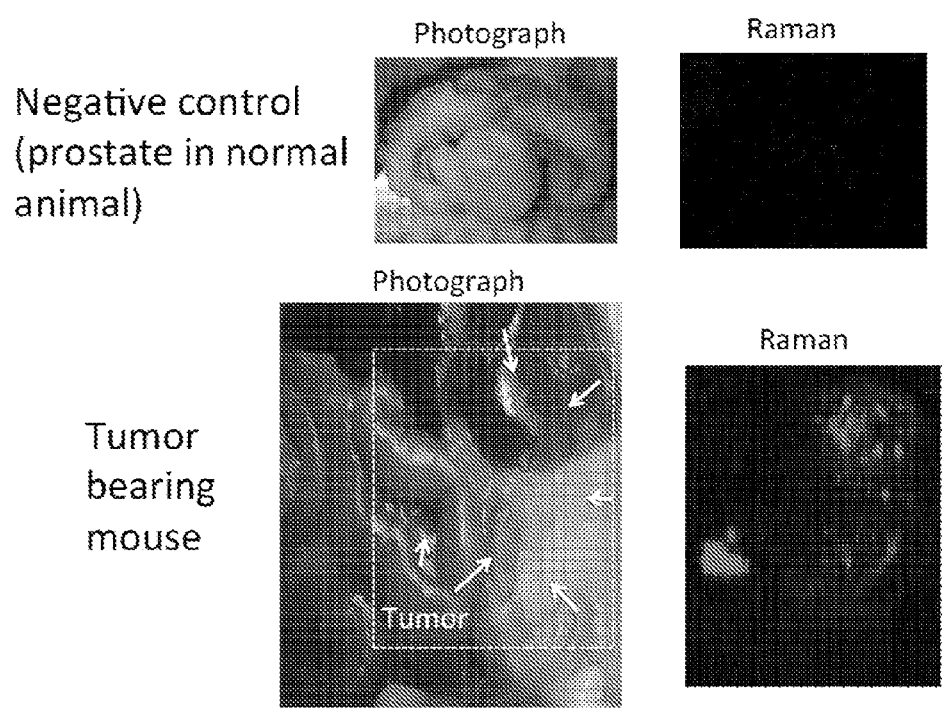
FIG. 13 shows a series of images illustrating using MPR-Nanostars nanoparticles for detecting prostate cancer. The depicted experiment was performed in a state-of-the-art genetic spontaneous (Hi-Myc) mouse model of prostate cancer. Mice express human c-Myc in the mouse prostate. The upper row of images shows a control animal (same mouse strain but without the Myc mutation) that was injected with MPR-Nanostars: No Raman signal is seen in this normal prostate. The lower row of images shows images from a prostate cancer bearing mouse (hi-Myc) with obvious deformity of the prostate due to tumor (photograph) that was injected with the same amount of MPR-Nanostars. The Raman image shows accumulation of MPR-Nanostars within the tumor areas.
Figure 14:
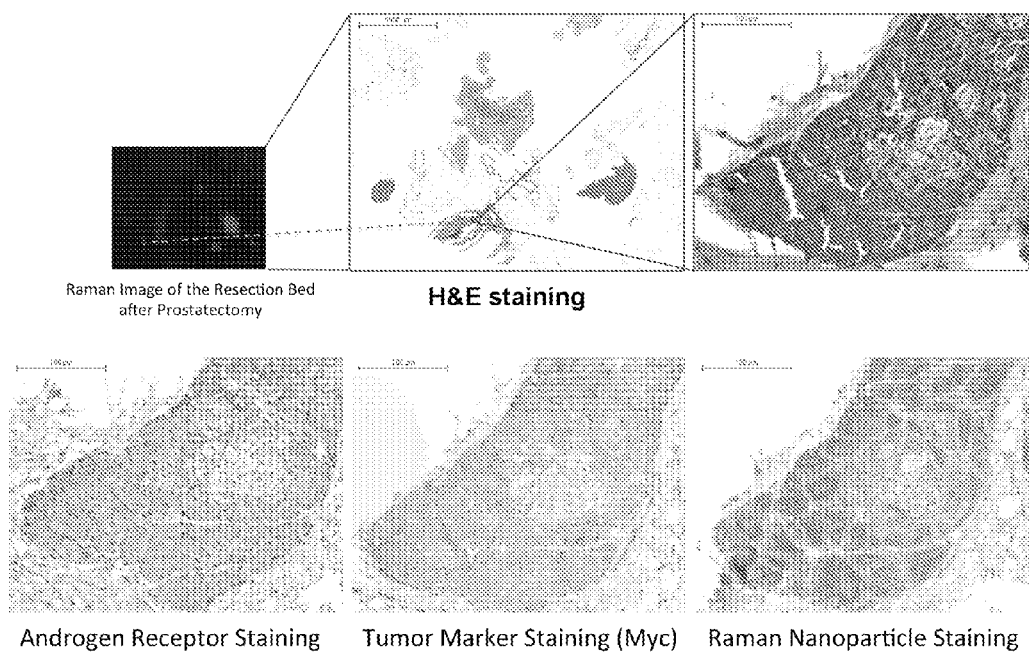
FIG. 14 shows a series of images illustrating using MPR-Nanostars for detecting microscopic residual tumor in resection bed in a transgenic mouse model of prostate cancer (Hi-Myc). A prostatectomy was performed in a tumor-bearing Hi-Myc mouse, and subsequently the resection bed was scanned with Raman imaging. Immunohistochemical correlation shows that small foci of Raman signal correspond to residual microscopic prostate cancer that could not have been visualized otherwise and would have been "missed". Note the excellent correlation between the histological tumor markers and the presence of the nanoparticles ("Raman nanoparticle staining"=antibody against PEGylated silica nanoparticle surface).
Figure 15:
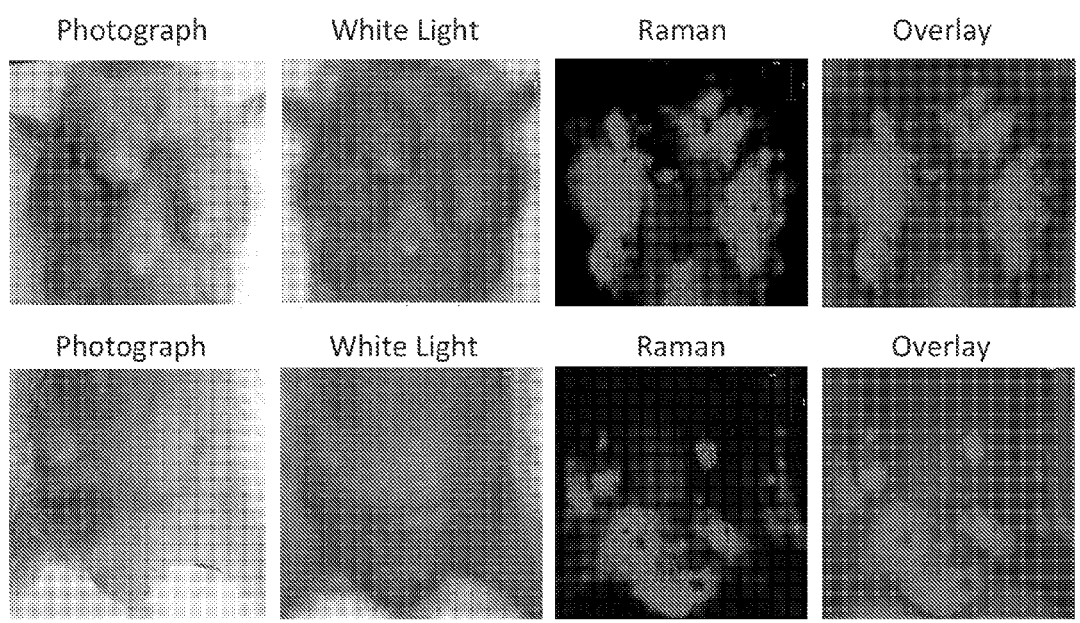
FIG. 15 shows a series of images of the use of MPR-Nanostars for detecting breast cancer in a state-of-the-art genetic MMTV-PyMT breast cancer mouse model. Mice with this genetic mutation spontaneously develop multiple breast cancers in different mammary glands and closely mimic human breast cancer pathology. Note that the Raman signal from the MPR-Nanostars accurately depicts the extent of multiple 3-6 mm sized breast cancers in the same mice, including small submillimeter tumor extensions. The upper row shows images of breast cancers developed along the upper and middle mammary glands of a MMTV-PyMT mouse. The lower row shows breast cancers developed within the lower mammary glands of a MMTV-PyMT mouse.
Figure 16:
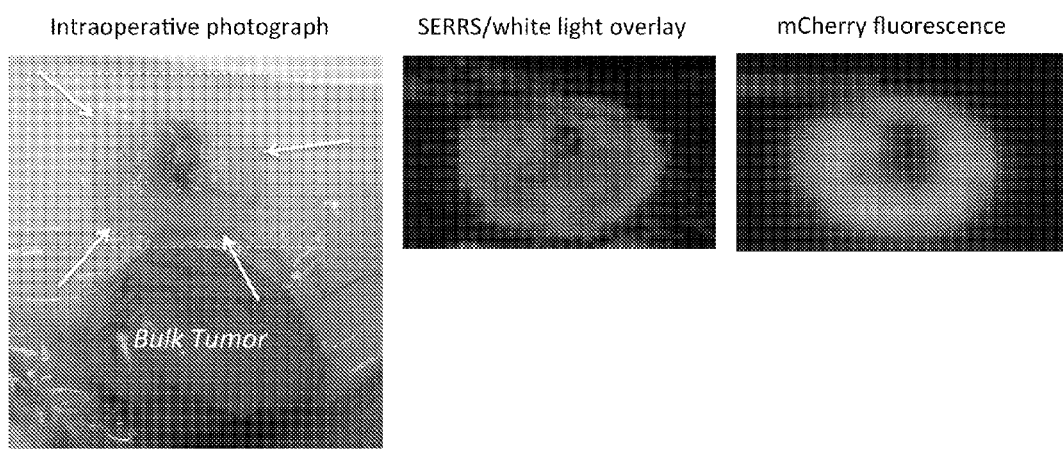
FIG. 16 shows a series of images of the use of MPR-Nanostars to detect microscopic tumor infiltration into the skin. This experiment was performed in an orthotopic 4T1 breast cancer mouse model. The 4T1 breast cancer cell line was transfected to express mCherry fluorescence. The photograph on the left shows the bulk tumor after the overlying skin was lifted off. Within the skin overlying the tumor, a subtle area of thickening was observed, with a central area of discoloration (arrows in dashed white box). We then performed Raman imaging of this area (middle image), which shows Raman signal outlining the area. The Raman signal matches closely the mCherry fluorescence (right image) emitted from the skin, proving the presence of breast cancer cells in this location.
Figure 17:
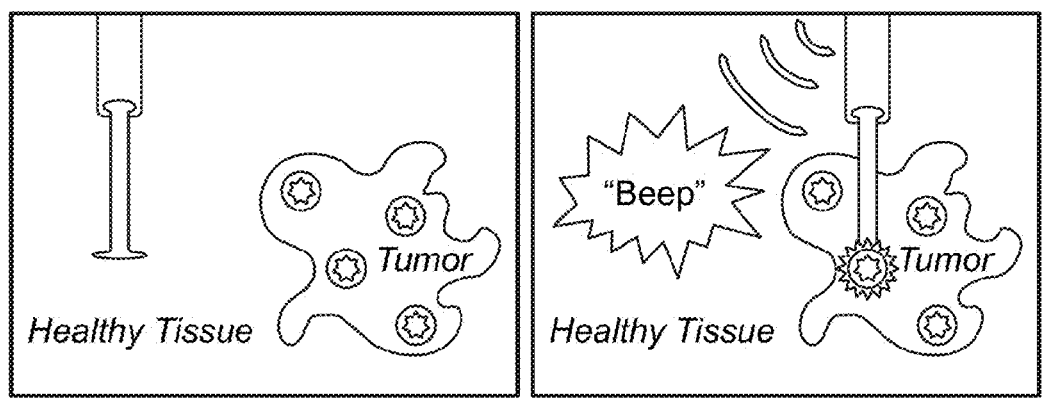
FIG. 17 illustrates the principle of hand-held Raman detection method as described in the Examples.
Figure 18:
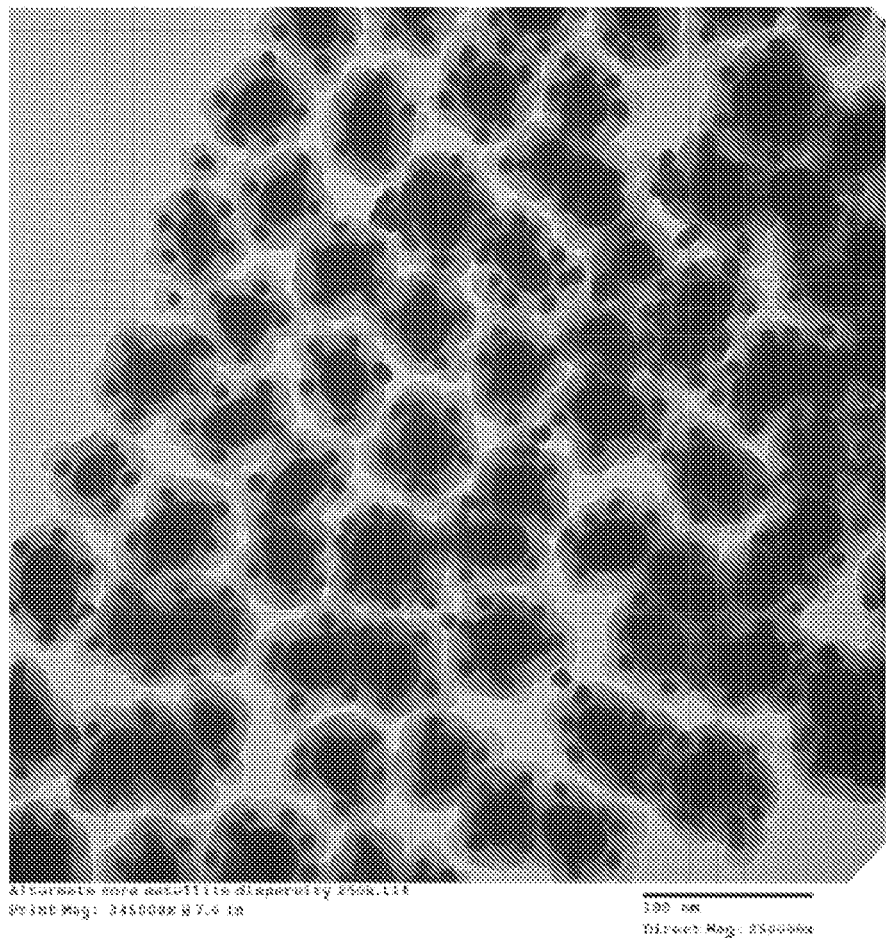
FIG. 18 shows a TEM of a population of representative SE(R)RS particles with a core-satellite configuration.
Figure 19:
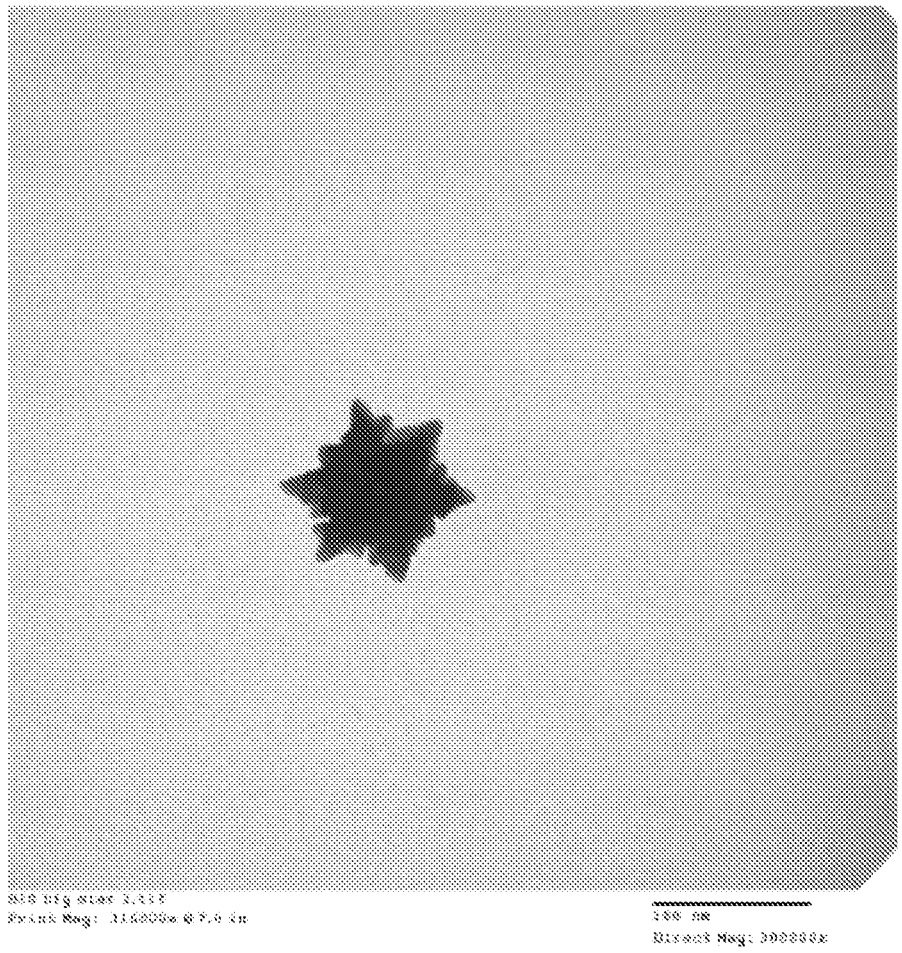
FIG. 19 shows a TEM of a representative fractal nanostar described in the present disclosure.
Figure 20:
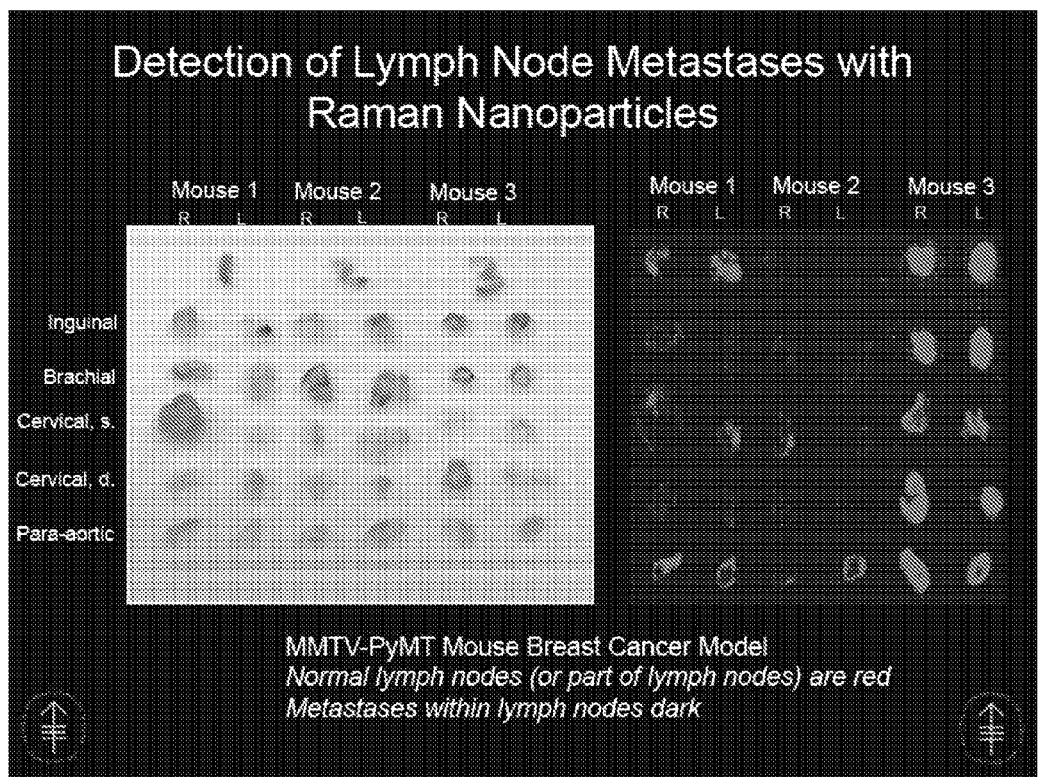
FIG. 20 shows images of lymph nodes that were resected from three different mice affected by metastatic breast cancer. The mice had been injected (via tail vein) with the SE(R)RS particles and mice were sacrificed after 24 hours and lymph nodes excised. "Clean" lymph nodes showed homogenous (resonant) Raman signal throughout the lymph node, while lymph nodes that contained metastatic breast cancer lesions (confirmed by histology) showed negative contrast.
Figure 21:
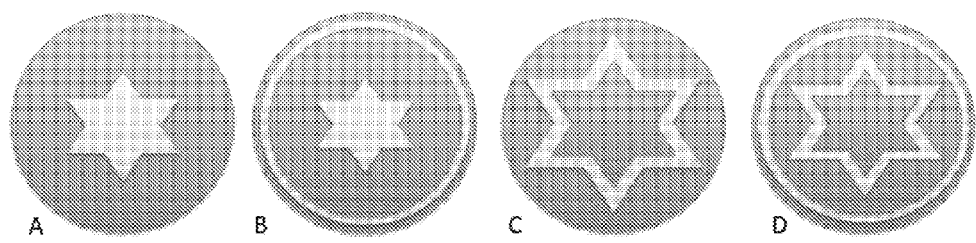
FIG. 21 illustrates exemplary particles with nanostar-based configurations in some embodiments of the present disclosure. A) solid gold star-shaped nanoscale core coated with a (resonant) agent-embedded encapsulant; B) solid gold star-shaped nanoscale core surrounded by (resonant) agent-embedded encapsulant, gold shell of a certain thickness and a encapsulant outer shell; C) gold star-shaped containing a (resonant) agent-embedded encapsulant collectively coated with an encapsulant; D) gold star-shaped shell containing (resonant) agent-embedded encapsulant surrounded by encapsulant (either with or without a resonant agent), a spherical gold shell and a encapsulant outer shell.
Figure 22:
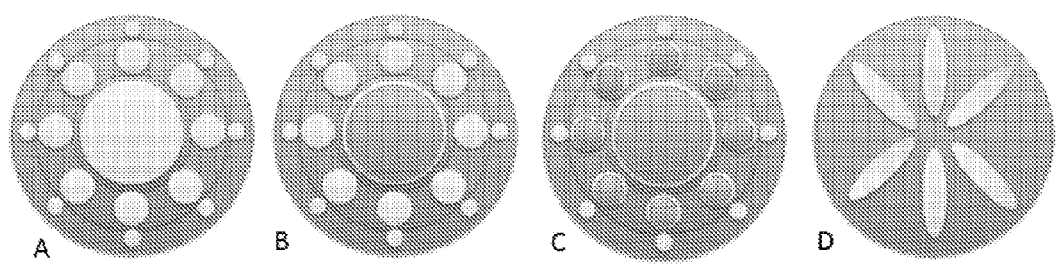
FIG. 22 illustrates exemplary particles with nanolens-based configurations in some embodiments of the present disclosure. A) solid gold sphere inner core surrounded by at least 1 layer of smaller sized spheres separated by ~5 nm (resonant) agent embedded encapsulant; B) gold spherical nanoshell inner core surrounded by at least 1 layer of smaller sized spheres separated by ~5 nm (resonant) agent embedded encapsulant; C) gold spherical nanoshell inner core surrounded by a smaller sized nanoshell separated by ~10 nm (resonant) agent embedded encapsulant with an outer shell consisting of solid particles embedded in an encapsulant; D) gold ellipse-shaped particles embedded in (resonant) agent containing an encapsulant.
Figure 23:
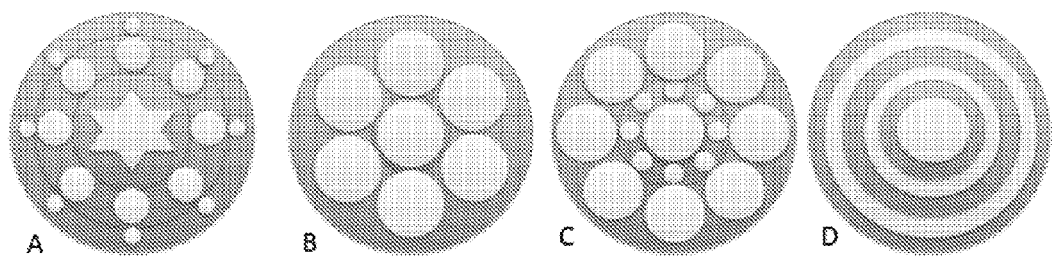
FIG. 23 illustrates exemplary particles in accordance with the present disclosure. A) solid gold star-shaped inner core surrounded by at least 1 layer of smaller sized spheres separated by ~10 nm (resonant) agent embedded encapsulant (and variations thereof); B) a nanorosette consisting of a solid gold nanoscale core surrounded by equally sized solid gold particles embedded in (resonant) agent containing encapsulant; C) gold spherical inner core surrounded by at least 1 layer of smaller sized spheres and 1 layer of larger gold nanospheres separated by ~10 nm (resonant) agent embedded encapsulant; D) nano-matryoshka with a solid gold nanoscale core surrounded by multiple (at least 2) alternating shells (resonant) agent containing encapsulant and gold or any other noble metal.
Figure 24:
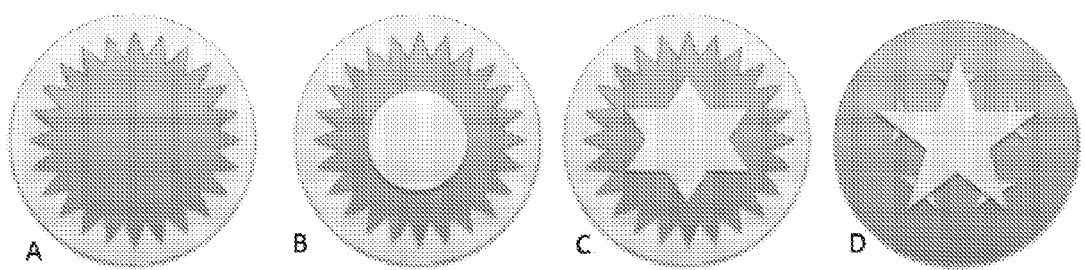
FIG. 24 illustrates exemplary particles with inverted nanostar configurations in some embodiments of the present disclosure. A) an inverted nanostar with a (resonant) agent embedded encapsulant core; B) an inverted nanostar with a solid spherical gold core embedded in (resonant) agent containing encapsulant; C) an inverted nanostar with a solid star-shaped gold core embedded in (resonant) agent containing encapsulant; D) a fractal nanostar embedded in (resonant) agent containing encapsulant.

Nanoparticle Tracking Analysis (NTA):

As shown in FIG. 3, the size distribution of 1 pM of particles in water is determined by NTA.

Example 3: Animal Tests

Referring to FIGS. 4-10, tumor-bearing mice (Dedifferentiated LipoSarcoma model, PyMT-MMTV (fvb) transgenic breast cancer model, Hi-MYC transgenic prostate cancer model, RCAS/TV-a transgenic glioma model) were injected with 150 uL 2.5 nM SE(R)RS particles synthesized in Example 1. Animals were sacrificed 18 hours or later and were scanned for Raman activity on the above described system. Tumor, organs and lymph nodes were harvested and subjected to ex vivo imaging additionally and subsequently wax embedded. The embedded tissues were processed for histology (H&E staining, tumor marker staining, macrophage staining).

Referring to FIGS. 11-16, MPR-Nanostars were used for detection of colon cancer, prostate cancer, and breast cancer in mice with histology correlation. The experiments further illustrated the use of MPR-Nanostars in a wide variety of different cancer models.

In Vivo-Ex Vivo Multimodal MRI-Raman-Histology Correlation:

We will demonstrate that SE(R)RS particles are able to depict the presence of tumor reliably and with microscopic precision in three different xenograft mouse sarcoma models (n=5 per model). The cells implanted in these mouse models are derived from actual human tumors. Mouse model #1 will be a dedifferentiated liposarcoma model, mouse model #2 a myxofibrosarcoma model, and mouse model #3 a pleomorphic malignant fibrous histiocytoma (FMH) model. All 3 models are known to produce local tumor infiltration and satellite micrometastases around the primary tumor. Model #2 and #3 are known to also produce metastases to lung and bone, and we will also assess the ability of our method to detect these distant metastases. We will inject the tumor bearing mice with the SE(R)RS particles (150 µl, 5 nM) intravenously; perform MRI after 24 hours; then sacrifice the animals and perform whole-body histological slicing using a macrotome (same slice thickness as MRI); then image these slices with our existing Raman microscope (Renishaw); and finally process the same slices histologically (H&E staining, tumor marker staining, macrophage staining) This will allow us to assess the precision of this multimodal SE(R)RS particle method, as we will be able to compare, on the same slices, the Raman signal with the MRI signal and the presence of tumor cells as proven by histology.

Biodistribution and Dose Finding Studies in Mice:

We will conduct in vivo PET-CT studies using SE(R)RS particles labeled with a PET tracer (zirconium-89, $^{89}$Zr). The labeling of SE(R)RS particles with $^{89}$Zr will be performed in collaboration with the Lewis lab at MSKCC. $^{89}$Zr-SE(R)RS particles will be injected intravenously into sarcoma bearing mice (n=3 for each tumor type above) and dynamic PET-CT imaging performed at 0, 1, 2, 4, 8, 12, 18, 24, 48 hours, 5 days, 7 days, 10 and 14 days. The PET data will provide A) an exact concentration of SE(R)RS particles within the tumors to allow calculation of the particle dosage used for aim 3, and B) determine the dynamics of intratumoral accumulation and retention of the SE(R)RS particles.

Testing of Raman-Guided Sarcoma Surgery in Dogs with Osteosarcoma:

We will demonstrate how sarcomas can be resected in large animals using the SE(R)RS particles and a hand-held Raman detector. The hand-held scanner has specifications very similar to our Renishaw benchtop Raman microscope, including the use of a laser with the same wavelength in the near-infrared (785 nm) and the same laser power of 300 mW. The hand-held particle can be held directly against the tissue of interest, and indicates with sound (or optical signal, if preferred) when it detects our SE(R)RS particles.

This aim will be performed in collaboration with the Animal Medical Center (AMC) located on $62^{nd}$ Street in Manhattan (http://www.amcny.org). This animal clinic is a highly specialized institution that routinely performs surgery on animals, including sarcoma surgeries. The incidence of osteosarcoma in dogs is high, and thus there will be a sufficient number of such diseased dogs where the owner will agree that surgery will be performed in conjunction with our image guidance method.

We will inject the SE(R)RS particles at the concentration determined in Aim 2 intravenously in the dogs (n=10). After 24 hours, animals will be anesthetized with isofluorane anesthesia. After sterile prepping of the animals the tumors will be surgically exposed and the bulk of the tumor that can be clearly identified by the surgeon with the naked eye will be resected. When the resection has progressed close to tumor margin, the hand-held Raman particle will be used to verify the presence of residual tumor and to search for the presence of local micrometastases in the surgical bed. If SE(R)RS particles are still present, the Raman scanner will notify the surgeon with a "beep" sound (see FIG. 17). The resection will then be continued until all Raman positive foci are resected; the resected tissue specimen will be sent for pathological evaluation (histology and tumor markers). Subsequently, another 5 cm rim of tissue (presumably tumor-free) will be resected and also sent for pathological evaluation in order to verify that the Raman guided surgery had indeed led to removal of all tumor cells.

Other Embodiments and Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition comprising nanoparticles, each of which comprises:
a nanoscale core comprising a metal or metal alloy;
a plurality of capping agent entities associated on the nanoscale core;
an outer silica encapsulant layer; and
a plurality of SE(R)RS-active agent dopant entities,
wherein the capping agent entities are characterized by sufficient affinity for the nanoscale core to provide stabilization sufficient to permit encapsulation of the nanoscale core by the outer silica encapsulant layer, while also being susceptible to displacement by the SE(R)RS-active agent dopant entities so that the SE(R)RS-active agent dopant entities are distributed at locations selected from the group consisting of: on or within the nanoscale core, on or between capping agent entities, on or within the outer silica encapsulant layer, and combinations thereof, and the composition is characterized in that when embedded in 1% agarose in well-plates and imaged, the composition has a detection threshold of or below 20 fM for Raman imaging.

2. The composition of claim 1, wherein the SE(R)RS-active agent dopant entities are distributed between or among capping agent entities on the core.

3. The composition of claim 1, wherein at least some of the SE(R)RS-active agent dopant entities are within the outer silica encapsulant layer.

4. The composition of claim 1, wherein at least some of the SE(R)RS-active agent dopant entities are positioned within 10 nm of a surface of the nanoscale core.

5. The composition of claim 1, wherein the composition has a detection threshold of or below 10 fM.

6. The composition of claim 1, wherein the nanoparticles of the composition are substantially free of a surface primer.

7. The composition of claim 1, wherein the nanoscale core is non-spherical.

8. The composition of claim 1, wherein the metal is selected from a group consisting of gold, silver, copper and combinations thereof.

9. The composition of claim 1, wherein the nanoparticles of the composition further comprise one or more therapeutic or imaging agents associated with the outer silica encapsulant layer.

10. The composition of claim 9, wherein the one or more agents are imaging agents selected from the group consisting of MRI agents, PET agents, SPECT agents, CT agents, and combinations thereof.

11. The composition of claim 10, wherein the MRI agent is selected from: Gd-salt, iron oxide, a paramagnetic CEST agent, and combinations thereof.

12. The composition of claim 9, wherein the one or more agents are directly associated on a surface of the outer silica encapsulant layer.

13. The composition of claim 12, wherein the one or more agents are indirectly associated on the surface of the outer silica encapsulant layer via a linker.

14. The composition of claim 1, wherein each of the nanoparticles has a diameter of about 1 nm to about 10 nm, or about 10 nm to about 300 nm.

15. A method of applying a silica encapsulant layer to a metal or metal alloy nanoscale core, the method comprising steps of:
providing a capped composition comprising:
a metal or metal alloy nanoscale core substantially coated with:
a first plurality of capping agent entities displaceably associated with the nanoscale core's surface;
contacting the capped composition with:
a plurality of SE(R)RS-active agent dopant entities; and
a plurality of encapsulant precursor entities,
the contacting being performed under conditions and for a time sufficient to permit:
accumulation of dopant entities onto or nearby the core surface; and
formation of an outer silica encapsulant layer by the encapsulant precursor entities such that a composition is generated that comprises:
a nanoscale core comprising a metal or metal alloy;
a second plurality of capping agent entities associated on the nanoscale core;
an outer silica encapsulant layer; and
a plurality of dopant entities,
wherein the capping agent entities are characterized by sufficient affinity for the nanoscale core to provide stabilization sufficient to permit encapsulation of the nanoscale core by the outer silica encapsulant layer, while also being susceptible to displacement by the dopant entities so that the dopant entities are distributed at locations selected from the group consisting of: on or within the core, on capping agent entities, within the outer silica encapsulant layer, on the outer silica encapsulating layer and combinations thereof, the generated composition being characterized in that when embedded in 1% agarose in well-plates and imaged, the generated composition has a detection threshold of or below 20 fM for Raman imaging.

16. The method of claim 15, wherein the step of providing comprises providing a capped composition that does not include the addition of any surface primer.

17. The method of claim 15, wherein the step of contacting does not include contacting with any surface primer.

18. A method comprising steps of administering to a subject a collection of particles each of which is comprised of:
a nanoscale core comprising a metal or metal alloy;
a plurality of capping agent entities associated on the core;
an outer silica encapsulant layer; and
a plurality of SE(R)RS-active agent dopant entities, wherein the capping agent entities are characterized by sufficient affinity for the nanoscale core to provide stabilization sufficient to permit encapsulation of the nanoscale core by the outer silica encapsulant layer, while also being susceptible to displacement by the SE(R)RS-active agent dopant entities so that the SE(R)RS-active agent dopant entities are distributed at locations selected from the group consisting of: on or within the nanoscale core, on capping agent entities, within the outer silica encapsulant layer, on the outer silica encapsulant layer and combinations thereof, wherein particles of the collection are characterized in that when embedded in 1% agarose well-plates and imaged, the particles of the collection have a detection threshold of or below 20 fM for Raman imaging.

19. The method of claim 18, wherein the subject has a solid tumor.

20. The method of claim 19, wherein the solid tumor is selected from the group consisting of brain, lung, breast, ovary, stomach, pancreas, larynx, esophagus, testes, liver, parotid, biliary tract, colon, rectum, cervix, uterus, endometrium, kidney, bladder, prostate, thyroid, head and neck, melanomas, gliomas, neuroblastomas, and neuroendocrine tumors.

21. The method of claim 19, wherein the step of administering comprises administering to a location and in an amount such that particles from the collection localize to the solid tumor.

22. The method of claim 18, wherein the particles further comprise a targeting entity.

23. The method of claim 18, wherein the nanoscale core is gold.

24. The method of claim 18, wherein the particles further comprise MM agents, PET agents, SPECT agents, CT agents, or any combinations thereof.

25. The method of claim 24, further comprising a step of imaging localized particles.

26. The method of claim 25, wherein the step of imaging comprises:
obtaining a MM or PET or SPECT or CT signal, wherein the signal is used to produce an image corresponding to one or more of: the localization of the whole tumor, macroscopic delineation of the whole tumor, and residual tumor;

obtaining a photoacoustic signal, wherein the photoacoustic signal is used to produce an image corresponding to the tumor with deep tissue penetration;

obtaining a Raman vibrational signal, wherein the Raman vibrational signal is used as a guide to defining the tumor margins; and producing an image of the tumor and the tumor margins using the MRI signal, photoacoustic signal, and Raman vibrational signal.

27. The composition of claim 1, wherein the detection threshold is 5 fM or less for Raman imaging.

28. The composition of claim 1, wherein the detection threshold is 1 fM or less for Raman imaging.

29. The composition of claim 1, wherein the detection threshold is measured in vivo.

30. The composition of claim 1, wherein the capping agent entities do not contain strongly-binding atoms.

31. The composition of claim 1, wherein the capping agent entities contain strongly-binding atoms, and the strongly-binding atoms are nitrogen or sulfur atoms.

32. The composition of claim 31, wherein the strongly-binding atoms are nitrogen atoms.

33. The composition of claim 31, wherein the strongly-binding atoms are sulfur atoms.

34. The composition of claim 30, wherein each of the nanoparticles does not include a surface primer that has greater affinity than the capping agent entities.

35. The composition of claim 1, wherein capping agent entities of the plurality are selected from the group consisting of citrate, ascorbic acid, ascorbate, palmitoylascorbate, tetrakis(hydroxymethyl)phosphonium chloride, amino acids and combinations thereof.

* * * * *